United States Patent [19]

Yagihara et al.

[11] Patent Number: 5,100,761

[45] Date of Patent: * Mar. 31, 1992

[54] SILVER HALIDE PHOTOGRAPHIC MATERIALS

[75] Inventors: Morio Yagihara; Hisashi Okada; Kazunobu Katoh; Noriyuki Inoue; Shingo Nishiyama; Tetunori Matushita, all of Kanagawa, Japan

[73] Assignee: Fuji Photo Film Co., Ltd., Kanagawa, Japan

[ * ] Notice: The portion of the term of this patent subsequent to Aug. 28, 2007 has been disclaimed.

[21] Appl. No.: 170,524

[22] Filed: Mar. 21, 1988

[30] Foreign Application Priority Data

Mar. 20, 1987 [JP] Japan .................. 62-67508
Mar. 20, 1987 [JP] Japan .................. 62-67509
Mar. 20, 1987 [JP] Japan .................. 62-67510

[51] Int. Cl.$^5$ .................. G03C 1/08; G03C 1/485
[52] U.S. Cl. .................. 430/264; 430/410; 430/596; 430/597; 430/598; 430/606; 430/940
[58] Field of Search .................. 430/264, 410, 598, 606, 430/940, 596, 597

[56] References Cited

U.S. PATENT DOCUMENTS

| | | | |
|---|---|---|---|
| 2,965,485 | 12/1960 | Duffin et al. | 96/101 |
| 3,910,795 | 10/1975 | Shiba et al. | 96/100 |
| 4,550,070 | 10/1985 | Miyasaka et al. | 430/202 |
| 4,737,452 | 4/1988 | Kameoka et al. | 430/600 |
| 4,820,625 | 4/1989 | Saeki et al. | 430/596 |
| 4,840,889 | 6/1989 | Uesawa et al. | 430/597 |
| 4,908,293 | 3/1990 | Katoh et al. | 430/264 |
| 4,952,483 | 8/1990 | Inoue et al. | 430/378 |

FOREIGN PATENT DOCUMENTS 0130856 1/1985 European Pat. Off. .
0154293 9/1985 European Pat. Off. .

OTHER PUBLICATIONS

Research Disclosure, No. 235, Nov. 1983, pp. 346-352.
European Search Report.

Primary Examiner—Charles L. Bowers, Jr.
Assistant Examiner—Janis L. Dote
Attorney, Agent, or Firm—Sughrue, Mion, Zinn, Macpeak & Seas

[57] ABSTRACT

A silver halide photographic material comprising one or more silver halide emulsion layers and hydrophilic colloid layers, wherein at least one of the layers contains an acylhydrazine compound as described below. The instant photographic materials have high contrast negative-gradation or positive-gradation characteristics, high maximum image density, excellent reversal characteristics and long-term storage stability.

23 Claims, No Drawings

SILVER HALIDE PHOTOGRAPHIC MATERIALS

FIELD OF THE INVENTION

This invention relates to a silver halide photographic material giving very high contrast and high sensitive negative images having good dot image quality. The invention also relates to a silver halide photographic material forming direct positive photographic images. In particular, the invention relates to a silver halide photographic material containing a novel compound as a nucleating agent for silver halide.

BACKGROUND OF THE INVENTION

Silver halide emulsions or developers containing a hydrazine compound are disclosed in U.S. Pat. No. 3,730,727 (a developer containing ascorbic acid and hydrazine), U.S. Pat. No. 3,227,552 (use of hydrazine as an auxiliary developing agent for obtaining direct positive color images), U.S. Pat. No. 3,386,831 (a silver halide photographic material containing a β-monophenylhydrazide of an aliphatic carboxylic acid as a stabilizer therefor), U.S. Pat. No. 2,419,975 and Mees, *The Theory of Photographic Process*, 3rd edition, page 281 (1966).

In particular, U.S. Pat. No. 2,419,975 discloses that high contrast negative images are obtained by the addition of hydrazine compounds. The aforesaid patent describes that very high contrast photographic characteristics are obtained by adding a hydrazine compound to a silver chlorobromide emulsion and developing it with a developer having a high pH of 12.8. However, the strong-alkaline developer having a pH of about 13 is unstable because it is easily air-oxidized and can not endure long-term storage and use.

Very high contrast photographic characteristics having a gamma (γ) over 10 are very useful for the photographic reproduction of continuous tone images by dot images useful for making printing plates or the reproduction of line images. For such a purpose, a process of using a silver chlorobromide photographic emulsion having a silver chloride content of over 50 mole %, and more preferably over 75 mole % and developing it with a hydroquinone developer having a very low effective concentration (usually lower than 0.1 mole/liter) of sulfite ion is generally used. However, since in the aforesaid process, the sulfite ion concentration of the developer is low, the developer is very unstable and can not endure storage for over 3 days.

Furthermore, since the aforesaid process requires the use of a silver chlorobromide emulsion having a relatively high silver chloride content, the process can not give high sensitivity. Accordingly, it has been strongly desired to obtain high contrast photographic characteristics useful for the reproduction of dot images and line images using a high speed silver halide emulsion and a stable developer.

The present inventors have found that the acylhydrazine compounds used for silver halide photographic emulsions giving very high contrast negative photographic characteristics using a stable developer disclosed in U.S. Pat. Nos. 4,224,401, 4,168,977, 4,243,739, 4,272,614, 4,323,643, etc., have various defects.

For example, it is known that these conventional hydrazines generate nitrogen gas during development which forms bubbles in the photographic film during processing to damage the photographic images formed. Furthermore, the hydrazine compounds flow out into the developer solution during processing which adversely affect the quality of the other photographic materials.

Also, these prior art hydrazines are required to be used in a large amount thereof to obtain high sensitivity and high contrast. Further, when the hydrazine is used in combination with other sensitizing techniques (e.g., enhancing a chemical sensitivity, enlarging grain size or, adding compound accelerating sensitization as described in U.S. Pat. Nos. 4,272,606 and 4,241,164) in cases where a particularly high sensitivity is required in regard to the performance of photographic light-sensitive materials, the sensitization with the passage of time and the formation of fog by sensitization generally occur during the storage of the photographic light-sensitive materials.

Accordingly, compounds capable of reducing the generation of bubbles and their flow into a developer, giving no problem in long-term storage stability, and capable of giving very high contrast photographic characteristics by the addition of a very small amount thereof are desirable.

Also, it is disclosed in U.S. Pat. Nos. 4,385,108, 4,269,929 and 4,243,739 that very high contrast negative gradation photographic properties are obtained by using hydrazines containing a substituent capable of easily adsorbing onto silver halide grains. However, some of these hydrazines having the adsorptive substituent group cause the desensitization with the passage of time during the storage of the photographic light-sensitive materials containing the compounds. Accordingly, it is required to select hydrazine compounds that do not cause this problem.

On the other hand, there are various direct positive photographic processes, and among them, a process of light-exposing a silver halide emulsion containing previously fogged silver halide grains in the presence of a desensitizer and then developing the emulsion and a process of light-exposing a silver halide emulsion having sensitive specks mainly in the silver halide grains and then developing the emulsion in the presence of a nucleating agent are most useful. The present invention relates to photographic light-sensitive materials for use in the latter process. The aforesaid silver halide emulsion having sensitive specks mainly in the interior of silver halide grains and forming latent images mainly in the interior of the silver halide grains is referred to as "internal latent image type silver halide emulsion" and shall be distinguished from a silver halide emulsion forming latent images mainly on the surface of the silver halide grains.

A process of obtaining direct positive image by surface-developing the internal latent image type silver halide photographic emulsion in the presence of a nucleating agent and silver halide photographic emulsions and photographic light-sensitive materials which are used for the process are known.

In the aforesaid process of obtaining direct positive images, the nucleating agent may exist in the developer. However, when the nucleating agent is incorporated in either the silver halide photographic emulsion layer or other proper layer of the photographic light-sensitive material and adsorbed on the surface of the silver halide grains therein, good reversal characteristics can be obtained.

As the nucleating agent which is used for the aforesaid process of obtaining direct positive images, there are hydrazine and hydrazine series compounds described in U.S. Pat. Nos. 2,563,785 and 2,588,982; hydrazide and hydrazine series compounds described in U.S. Pat. No. 3,227,552; heterocyclic quaternary salt compounds described in U.S. Pat. Nos. 3,615,615, 3,719,494, 3,734,738, 4,094,683 and 4,115,122, British Patent 1,283,835, Japanese Patent Application (OPI) Nos. 3426/77 and 69613/77 (the term "OPI" as used herein indicates an "unexamined published application"); thiourea bond-type acylphenylhydrazine series compounds described in U.S. Pat. Nos. 4,030,925, 4,031,127, 4,139,387, 4,245,037, 4,255,511 and 4,276,364, and British Patent 2,012,443; compounds gaving a heterocyclic thioamide as an adsorptive group described in U.S. Pat. No. 4,080,207; phenylhydrazine compounds having a heterocyclic group having a mercapto group as an adsorptive group described in British Patent 2,011,397; sensitizing dyes having a substituent showing a nucleating action in the molecular structure thereof described in U.S. Pat. No. 3,718,470, and hydrazine compounds described in Japanese Patent Application (OPI) Nos. 200230/84, 212828/84, and 212,829/84, and *Research Disclosure*, No. 23510 (November, 1953).

However, it has been confirmed that these compounds have the following disadvantages. That is, some of these compounds are insufficient in activity as nucleating agent; some of the compounds are insufficient in storage stability although the activity is high; some of the compounds decrease the activity thereof after being added to a silver halide emulsion and before coating; also, some of the compounds deteriorate the layer quality when a large amount thereof is added to the emulsion layer.

For solving the aforesaid problems, hydrazine derivatives such as adsorption-type hydrazine derivatives, etc., are proposed in Japanese Patent Application (OPI) Nos. 179734/85, 170733/86, 65034/87, and 270744/86 and Japanese Patent Application No. 19,739/85 and a considerable improvement has been achieved by using these hydrazine derivatives. However, the activity as nucleating agent is insufficient for the requirement of lowering the pH of a developer for increasing the stability of the developer (i.e., preventing the deterioration of the developing agent in the developer) or shortening the developing time.

SUMMARY OF THE INVENTION

Therefore, a first object of this invention is to provide a silver halide photographic material capable of providing very high contrast negative-gradation photographic characteristics having a gamma of over 10 using a stable developer.

A second object of this invention os to provide a negative working silver halide photographic material containing a highly active acylhydrazine capable of giving desired very high contrast negative-gradation photographic characteristics even by using a developer having a low pH with the addition of a small amount of the acylhydrazine without adversely influencing the other photographic characteristics.

A third object of this invention is to provide a direct positive-type silver halide photographic material containing a highly active acylhydrazine capable of giving excellent reversal characteristics even by using a developer having a low pH.

A fourth object of this invention is to provide a silver halide photographic material containing an acylhydrazine, which can be easily synthesized and has excellent long-term storage stability.

It has now been discovered that the aforesaid various objects can be attained by the present invention as set forth below.

That is, according to this invention, there is provided a silver halide photographic material having a least one silver halide photographic emulsion layer, wherein the silver halide photographic emulsion layer or at least one hydrophilic colloid layer contains at least one compound represented by general formulas (I), (II) or (III) described below;

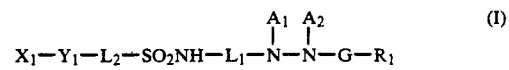

wherein $A_1$ and $A_2$ both represent a hydrogen atom or one of $A_1$ and $A_2$ represents a hydrogen atom and the other represents a sulfinic acid residue or an acyl group; $R_1$ represents a hydrogen atom, an alkyl group, an aryl group, an alkoxy group, an aralkyl group, an aryloxy group, or an amino group, further providing that these groups may be substituted; G represents a carbonyl group, a sulfonyl group, a sulfoxy group, a phosphoryl group or an iminomethylene group which may have an N-substituent; $L_1$ represents an arylene group; $L_2$ represents a divalent linkage group; $Y_1$ represents $-NR_2CONR_3-$ (whrein $R_2$ and $R_3$, which may be the same or different, each represents a hydrogen atom or an alkyl group) or $-SO_2NR_4-$ (wherein $R_4$ represents a hydrogen atom or an alkyl group); and $X_1$ represents an adsorption accelerating group for silver halide;

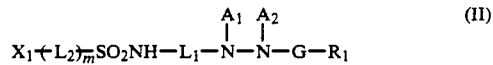

wherein $A_1$ and $A_2$ both represent a hydrogen atom or one of $A_1$ and $A_2$ represents a hydrogen atom and the other represents a sulfinic acid residue or an acyl group; $R_1$ represents a hydrogen atom, an alkyl group, an aryl group, an alkoxy group, an aralkyl group, an aryloxy group, or an amino group; G represents a carbonyl group, a sulfonyl group, a sulfoxy group, a phosphoryl group or an iminomethylene group; $L_1$ represents an arylene group; $L_2$ represents a divalent linkage group; $X_1$ represents an adsorption accelerating group for silver halide; and m represents 0 or 1;

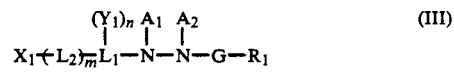

wherein $A_1$ and $A_2$ both represent a hydrogen atom or one of $A_1$ and $A_2$ represents a hydrogen atom and the other represents a sulfinic acid residue or an acyl group; $R_1$ represents a hydrogen atom, an alkyl group, an aryl group, an alkoxy, group, an aralkyl group, an aryloxy group, or an amino group; G represents a carbonyl group, a sulfonyl group, a sulfoxy group, a phosphoryl group, or an iminomethlene group; $L_1$ represents an arylene group having $Y_1$ as a substituent; $L_2$ represents a divalent linkage grooup; $X_1$ represents an adsorption accelerating group for silver halide; $Y_1$ represents a substituent capable being dissociated into an anion having a pKa of at least 6 or an amino group; m represents 0 or 1; and n represents 1 or 2.

DETAILED DESCRIPTION OF THE INVENTION

In formula (I), $A_1$ and $A_2$ both are a hydrogen atom or one of them is a hydrogen atom and the other is an alkylsulfonyl group having not more than 20 carbon atoms, an arylsulfonyl group (preferably a phenylsulfonyl group or a phenylsulfonyl group substituted so that the sum of the Hammett's substituent constants becomes at least −0.5), or an acyl group having not more than 20 carbon atoms (preferably a benzoyl group, a substituted benzoyl group so that the sum of the Hammett's substituent constants becomes at least 0.5, or a straight chain, branched, or cyclic unsubstituted or substituted aliphatic acyl group wherein the substituent can be a halogen atom, an ether group, a sulfonamide group, a carbonamido group, a hydroxyl group, a carboxyl group, and a sulfonic acid group). The most preferably, $A_1$ and $A_2$ are simultaneously hydrogen atom.

G and $R_1$ in formula (I) are as follows.

When G is a carbonyl group, $R_1$ is preferably a hydrogen atom, an alkyl group (e.g., a methyl group, a trifluoromethyl group, a 3-hydroxypropyl group, or a 3-methanesulfonamidopropyl group), an aralkyl group (e.g., 4,0-hydroxybenzyl group) or an aryl group (e.g., a phenyl group, a 3,5-dichlorophenyl group, an o-methanesulfonamidophenyl group, or a 4-methanesulfonylphenyl group), and more preferably a hydrogen atom.

When G is a sulfonyl group, $R_1$ is preferably an alkyl group (e.g., a methyl group), an aralkyl group (e.g., an o-hydroxyphenylmethyl group), an aryl group (e.g., a phenyl group), or a substituted amino group (e.g., a dimethylamino group).

When G is a sulfoxy group, $R_1$ is preferably a cyanobenzyl group or a methylthiobenzyl group.

When G is a phosphoryl group, $R_1$ is preferably a methoxy group, an ethoxy group, a butoxy group, a phenoxy group, or a phenyl group, and is more preferably a phenoxy group.

When G is an N-substituted or unsubstituted iminomethylene group, $R_1$ is a methyl group, an ethyl group, or a substituted or unsubstituted phenyl group.

Examples of the substituent for $R_1$ are an alkyl group, an aralkyl group, an alkoxy group, an aryl group, a substituted amino group, an acylamino group, a sulfonylamino group, a ureido group, a urethane group, an aryloxy group, a sulfamoyl group, a carbamoyl group, an aryl group, an alkylthio group, an arylthio group, a sulfonyl group, a sulfinyl group, a hydroxyl group, a halogen atom, a cyano group, a sulfo group, a carboxyl group, an acyloxy group, an acyl group, an alkyloxycarbonyl group, an aryloxycarbonyl group, an alkenyl group, an alkinyl group, and a nitro group. These groups may be further substituted.

Also, these groups may combine with each other to form a ring.

In this case, G is most preferably a carbonyl group.

Practical examples of the arylene group shown by $L_1$ are a phenylene group and a naphthylene group and these groups may be substituted by the substituent as exemplified above in regard to $R_1$. $L_1$ is preferably a phenylene group.

The divalent linkage group shown by $L_2$ is an atom or an atomic group including at least one of C, N, S, and O and is usually an alkylene group, an alkenylene group, an alkynylene group, an arylene group, —O—, —S—, —NH—, —N=, —CO—, —SO$_2$—, etc., (these groups may be substituted) singly or as a combination thereof. Examples of the divalent linkage group are

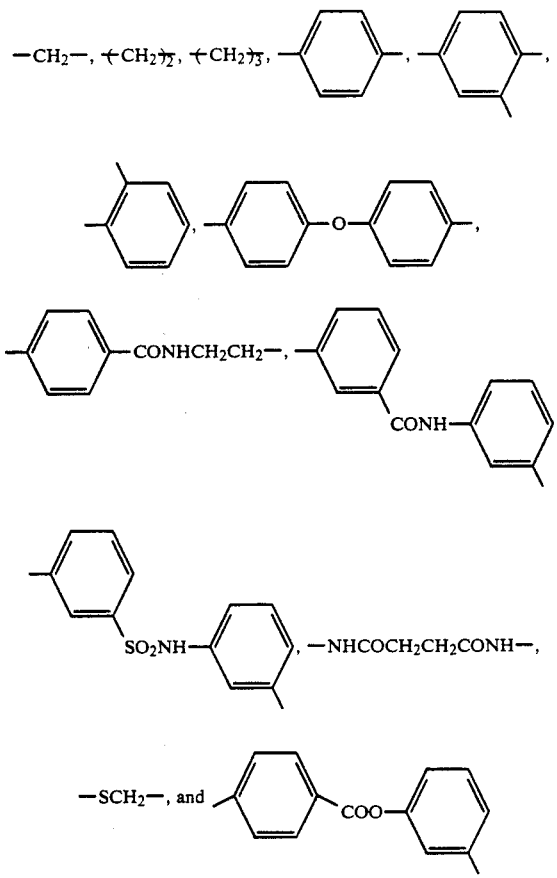

These groups may be substituted by a substituent as exemplified above as the substituents for $R_1$.

The alkyl group represented by $R_2$, $R_3$, and $R_4$ of —NR$_2$CONR$_3$— and —SO$_2$NR$_4$— shown by $Y_1$ is preferably a lower alkyl group having from 1 to 4 carbon atoms.

Preferred examples of the adsorption accelerating group for silver halide represented by $X_1$ are a thioamide group, a mercapto group and a 5- or 6-membered nitrogen-containing heterocyclic group.

The thioamide adsorption accelerating group shown by $X_1$ is a divalent group represented by

which may be a part of a ring structure or may be an acyclic thioamide group. Examples of the useful thiamide adsorption accelerating groups are described in U.S. Pat. Nos. 4,030,925; 4,031,127, 4,080,207, 4,245,037, 4,255,511, 4,266,013, and 4,276,364, *Research Disclosure*, Vol. 151, No. 15162 (November, 1976) and R.D., Vol. 176, No. 17626 (December, 1978).

Examples of the acylic thioamide group are a thioureido group, a thiourethane group and a dithiocarbamic acid ester group. Examples of the cyclic thioamide group are 4-thiazoline-2-thione, 4-imidazoline-2-thione, 2-thiohydrantoin, rhodanine, thiobarbituric acid, tetrazoline-5-thione, 1,2,4-triazoline-3-thione, 1,3,4-thiadiazoline-2-thione, 1,3,4-oxazoline-2-thione, benzimidazoline-2-thione, benzoxazoline-2-thione, and benzothioazoline-2-thione and they may be further substituted.

Examples of the mercapto group represented by $X_1$ include an aliphatic mercapto group, an aromatic mercapto group, and a heterocyclic mercapto group (when the atom adjacent to the nitrogen atom bonded to —SH group is a nitrogen atom, the heterocyclic mercapto group has the same meaning as the cyclic thioamide group which is in a tautomeric relation therewith).

As the 5- or 6-membered nitrogen-containing heterocyclic group represented by $X_1$, there are 5- or 6-membered nitrogen-containing heterocyclic rings composed of a combination of nitrogen, oxygen, sulfur and carbon. Preferred examples thereof are benzotriazole, triazole, tetrazole, indazole, benzimidazole, imidazole, benzothiazole, thiazole, benzoxazole, oxazole, thiadiazole, oxadiazole, and triazine. They may be further substituted by a proper substituent as exemplified above for $R_1$.

$X_1$ is preferably a cyclic thioamide group (e.g., a mercapto-substituted nitrogen-containing heterocyclic group such as, for example, a 2-mercaptothiadiazole group, a 3-mercapto-1,2,4-triazole group, a 5-mercaptotetrazole group, a 2-mercapto-1,3,4-oxadiazole group, and a 2-mercaptobenzoxazole group) or a nitrogen-containing hetero cyclic group (e.g., a benzotriazole group, a benzimidazole group, and an indazole group), and is more preferably a 5-mercaptotetrazole group.

Preferred compounds of the compounds represented by general formula (I) are represented by general formula (I').

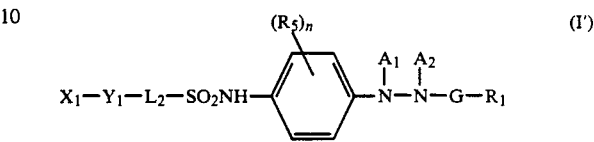

wherein $R_5$ represents a substituent group which is the same as the substituents exemplified above for $R_1$ of formula (I), $R_1$, G, $A_1$, $A_2$, $L_2$, $Y_1$, and $X_1$ have the same meaning as described above for formula (I), and n represents 0, 1 or 2.

Specific examples of the compound shown by formula (I) are illustrated below but the invention is not limited to these compounds.

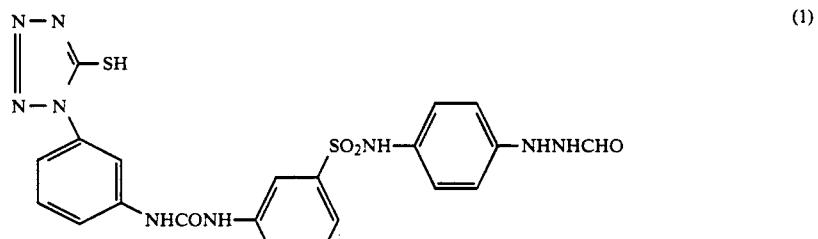

(1)

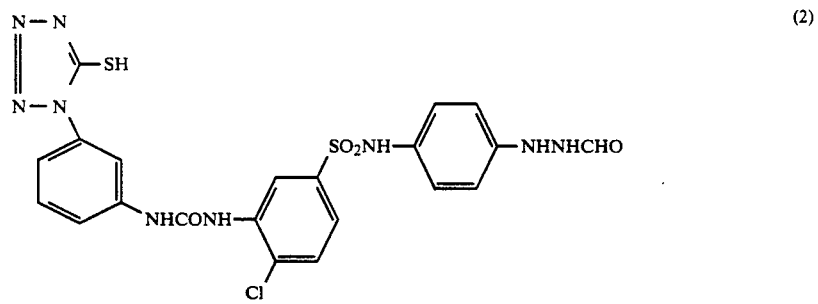

(2)

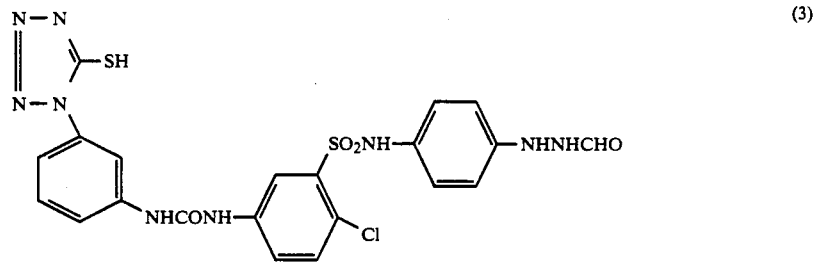

(3)

-continued
(4)
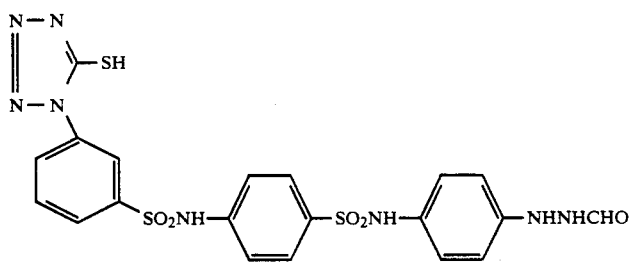
(5)
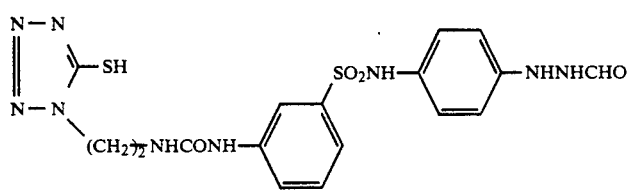
(6)
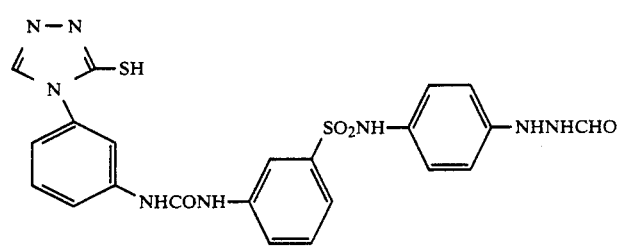
(7)
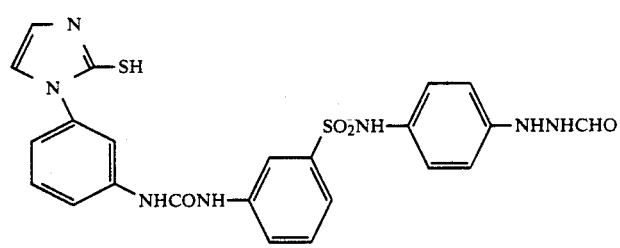
(8)
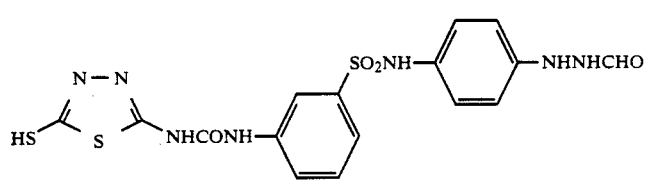
(9)
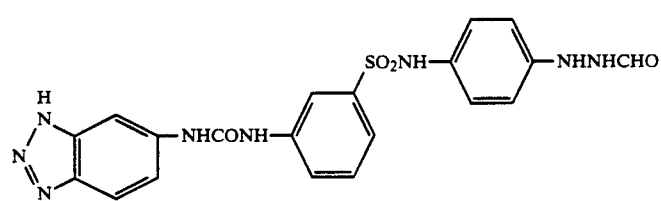
(10)
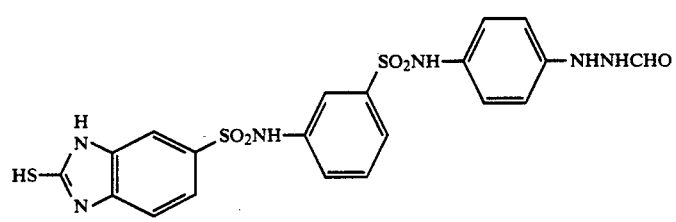

-continued
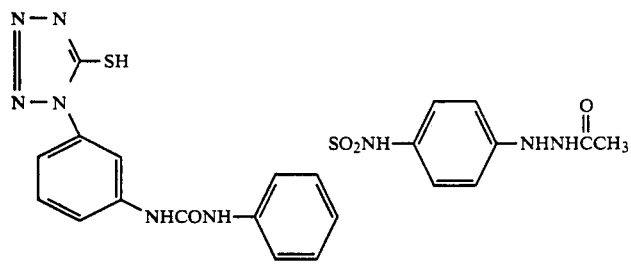
(11)
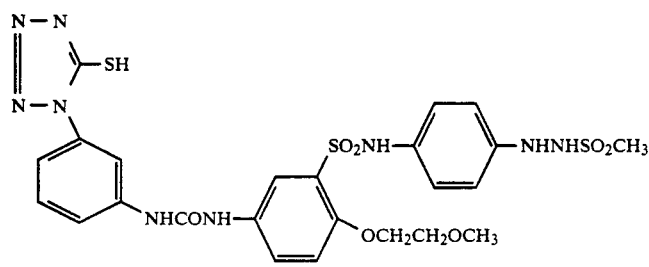
(12)
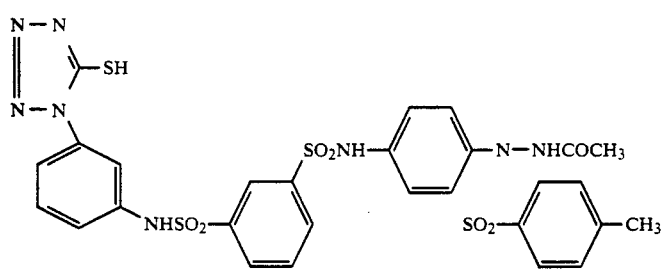
(13)
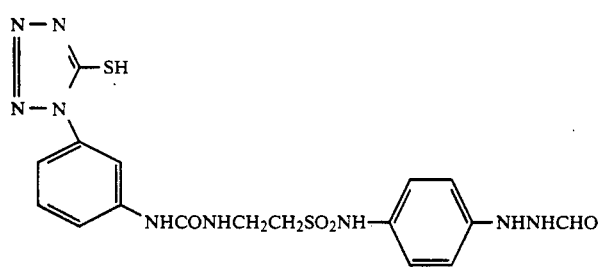
(14)
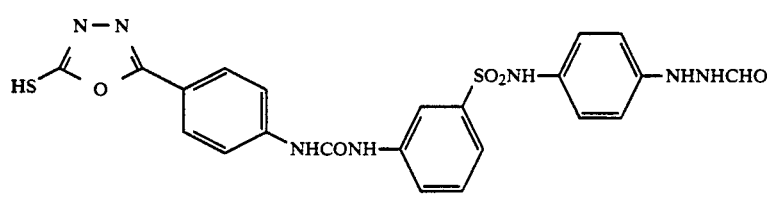
(15)
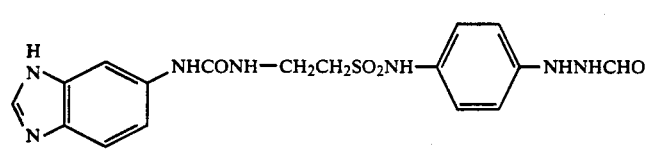
(16)

-continued
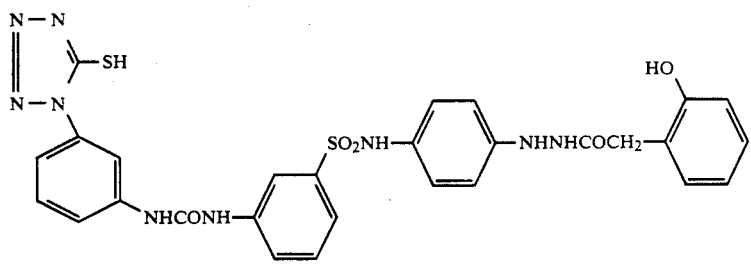
(17)
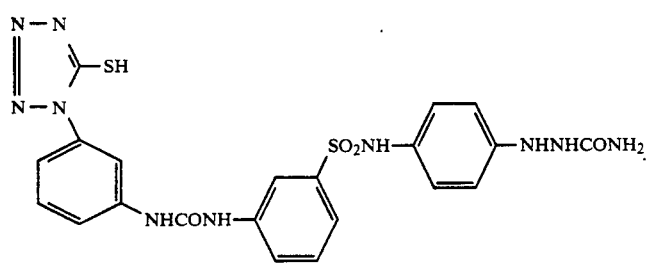
(18)
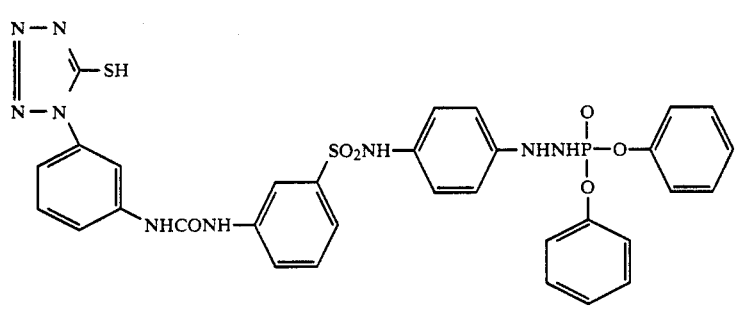
(19)
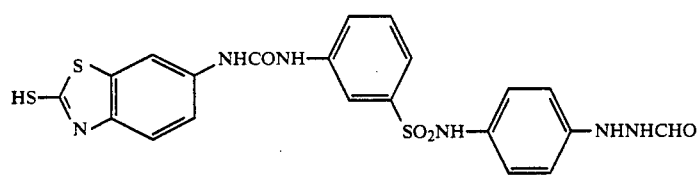
(20)
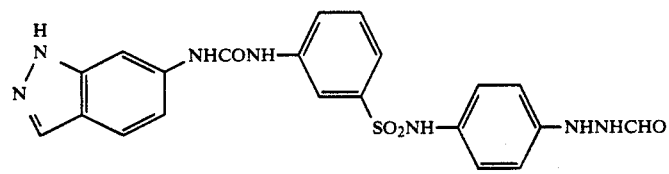
(21)
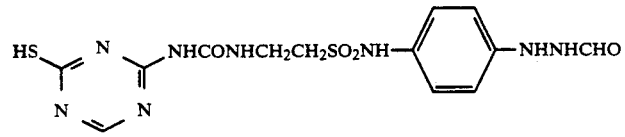
(22)
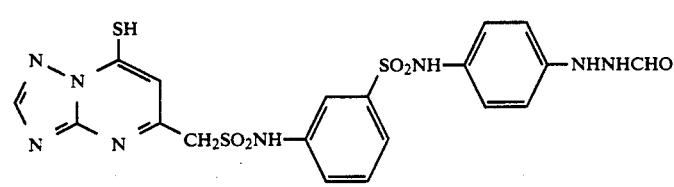
(23)

(24)

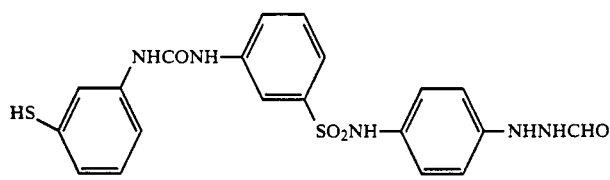

(25)

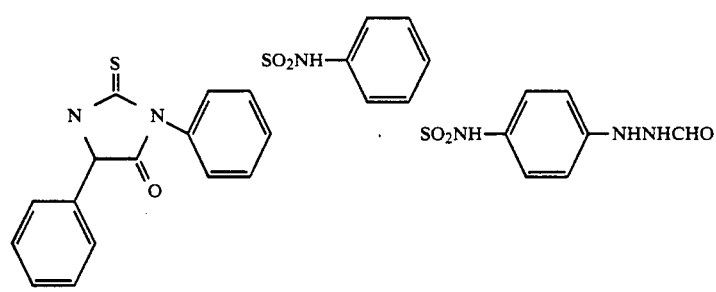

The compounds of formula (I) for use in this invention can be synthesized generally as follows.

Reaction A

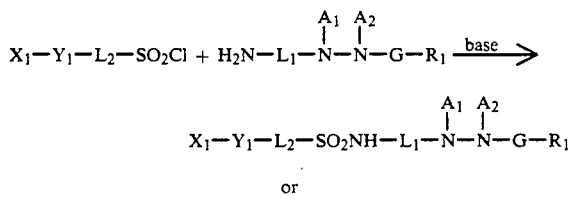

or

Reaction B
(e.g., when $Y_1$ is $NR_2CONR_3$)

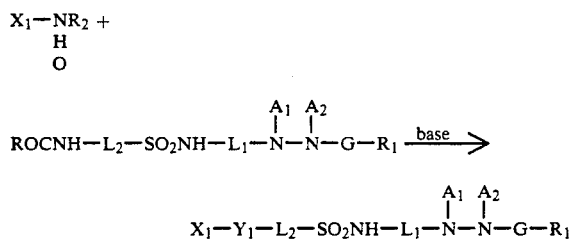

For these reactions, a solvent such as acetonitrile, tetrahydrofuran, dioxane, methylene chloride, chloroform, dimethylformamide, dimethylacetamide, etc., can be used; also triethylamine, N-ethylpiperidine, N-methylmorpholine, pyridine, imidazole, etc., can be used as the base.

Then, typical synthesis processes for the compounds of formula (I) are explained below.

Synthesis Example 1 Synthesis of Compound (1) 1-(1) Synthesis of 2-[4-(3)-nitrobenzenesulfonamido)-phenyl]-1-formylhydrazine In 1 liter of N,N-dimethylacetamide, 880 ml of acetonitrile and 285 g of triethylamine were dissolved 426 g of 2-(4-aminophenyl)-1-formylhydrazine in a nitrogen gas atmosphere and after cooling the mixture to −5° C., 625 g of m-nitrobenzenesulfonyl chloride were gradually added while cooling and with stirring so that the liquid temperature was not over −5° C. After further stirring the mixture for 1.5 hours at temperature below −5° C., the reaction mixture was extracted with 12 liters of ethyl acetate and 12 liters of a saturated aqueous sodium chloride solution at room temperature. The organic layer formed was collected and after concentrating it to 6 liters, 3 liters of n-hexane were added thereto followed by stirring for 30 minutes at room temperature. Then, crystals thus formed were collected by filtration and washed with 500 ml of ethyl acetate to provide 680 g of the desired product having a melting point of from 191° C. to 193° C.

1-(2) Synthesis of 2-[4-(3-aminobenzensulfonamido)-phenyl]-1-formylhydrazine

A mixture of 680 g of iron powder, 68 g of ammonium chloride, 6.5 liters of isopropanol, and 2.2 liters of water was heated on a steam bath with stirring. Then, 680 g of the nitro compound obtained in above step 1-(1) were added to the mixture and the resultant mixture was further refluxed for 1.5 hours. Then insoluble matter was removed by filtration and the filtrate was concentrated under reduced pressure. Then, water was added thereto and the crystals formed were collected by filtration and washed with 1 liter of isopropanol to provide 535 g of the desired product having melting point of from 155° C. to 156° C.

1-(3) Synthesis of 2-[4-(3-phenoxyamidobenzenesulfonamido)phenyl]-1-formylhydrazine After dissolving 450 g of the amino compound obtained in above step 1-(2) in 2.8 liters of N,N-dimethylacetamide in a nitrogen gas atmosphere, the solution was cooled to below −5° C. and after adding thereto 120 ml of pyridine, 230 g of phenyl chloroformic acid were added dropwise to the mixture while cooling the mixture with stirring so that the liquid temperature was not over −5° C. After further stirring the mixture for one hour at temperature below −5° C., the reaction mixture obtained was added dropwise to 20 liters of a saturated aqueous sodium chloride solution followed by stirring for 30 minutes. The crystals thus formed were collected by filtration and then washed with 2 liters of water to provide 611 g of the desired product having melting point of from 195° C. to 197° C.

1-(4) Synthesis of Compound (1)

In 30 ml of acetonitrile were dissolved 5.93 g of 1-(3-aminophenyl)-5-mercaptotetrazole hydrochloride and 70.3 g of imidazole in a nitrogen gas atmosphere and then the solution was heated to 65° C. To the solution was added dropwise a solution of 10 g of the urethane compound obtained in above step 1-(3) dissolved in 58 ml of N,N-dimethylacetamide and then the mixture was heated to 65° C. with stirring for 1.5 hours. Then, after cooling the reaction mixture to 30° C., the reaction mixture was extracted with 240 ml of ethyl acetate and 240 ml of water and the aqueous layer thus formed was collected and poured into a diluted aqueous hydrochloric acid solution. Crystals thus formed were collected by filtration and washed with water to provide 8.2 g of Compound (1) having a melting point of from 205° C. to 207° C. (decompd.)

Synthesis Example 2 Synthesis of Compound (3)

2-(1) Synthesis of 2-[4-(2-chloro-5-nitrobenzenesulfonamido)phenyl]-1-formylhydrazine In a mixture of 90 ml of N,N-dimethylacetamide, 76 ml of acetonitrile, and 19 ml of pyridine were dissolved 35.4 g of 2-(4-aminophenyl)-1-formylhydrazine in a nitrogen gas atmosphere and after cooling the solution to $-5°$ C., 59.9 g of 2-chloro-5-nitrobenzenesulfonyl chloride were gradually added to the solution while cooling the solution with stirring so that the liquid temperature was not over $-5°$ C. After further stirring the mixture for 1.5 hours at a temperature below $-5°$ C., the reaction mixture was poured into 1 liter of a saturated aqueous sodium chloride solution at room temperature. Crystals thus formed were collected by filtration and then washed with water to provide 63 g of the desired product.

2-(2) Synthesis of 2-[4-(5-amino-2-chlorobenzenesulfonamido)phenyl]-1-formylhydrazine A mixture of 30.1 g of iron powder, 4.5 g of ammonium chloride, 930 ml of dioxane, and 400 ml of water was heated on a steam bath with stirring. Then, 50 g of the nitro compound obtained in above step 2-(1) were added to the mixture and the resultant mixture was refluxed for 1.5 hours. Then, insoluble matter was filtered off and after concentrating the filtrate under reduced pressure, the reaction product was extracted with ethyl acetate and a saturated aqueous sodium chloride solution. Then, the organic layer thus formed was collected and concentrated under reduced pressure to provide 43 g of the desired product as an oily product.

2-(3) Synthesis of 1-(3-phenoxyamidophenyl)-5-mercaptotetrazole

In 800 ml of N,N-dimethylacetamide were dissolved 390.5 g of 1-(3-aminophenyl)-5-mercaptotetrazole hydrochloride, then after adding dropwise 302 ml of pyridine to the solution, the mixture was cooled to below 0° C., and then 235 ml of phenyl chloroformic acid was added dropwise to the mixture while cooling the mixture with stirring so that the liquid temperature was not over 0° C.

Then, after stirring the mixture for 30 minutes at temperature below 0° C., the temperature thereof was raised to room temperature followed by further stirring for 3 hours. After cooling the reaction mixture to below 10° C., 500 ml of isopropanol and 5 liters of water were added thereto followed by stirring for one hour, and crystals thus formed were collected by filtration and washed with water to provide 495 g of the desired product having a melting point of from 190° C. to 191° C.

2-(4) Synthesis of Compound (3)

In 35 ml of N,N-dimethylacetamide were dissolved 6.5 g of the amino compound obtained in above step 2-(2) and 5.4 g of the urethane compound obtained in above step 2-(3) in a nitrogen gas atmosphere and then 6.1 ml of N-methylmorpholine were added to the solution. After stirring the mixture for 7 hours at 50° C., the reaction mixture was cooled to room temperature and poured into 330 ml of diluted hydrochloric acid. Crystals thus formed were collected by filtration and washed with water to provide 6.2 g of Compound (3) having a melting point of from 160° C. to 165° C. (decompd.)

Synthesis Example 3 Synthesis of Compound (2)

3-(1) Synthesis of 2-[4-(4-chloro-3-nitrobenzenesulfonamido)phenyl]-1-formylhydrazine In a mixture of 90 ml of N,N-dimethylacetamide, 76 ml of acetonitrile, and 19 ml of pyridine were dissolved 35.4 g of 2-(4-aminophenyl)-1-formylhydrazine in a nitrogen gas atmosphere and after cooling the solution to $-5°$ C., 59.9 g of 4-chloro-3-nitrobenzenesulfonyl chloride were gradually added to the solution while cooling and with stirring so that the liquid temperature was not over $-5°$ C. After further stirring the mixture for 1.5 hours at a temperature below $-5°$ C., the temperature was raised to room temperature and the reaction mixture was poured into 1 liter of a saturated aqueous sodium chloride solution. Crystals thus formed were collected by filtration and washed with water to provide 67.5 g of the desired compound.

3-(2) Synthesis of 2-[4-(3-amino-4-chlorobenzenesulfonamido)phenyl]-1-formylhydrazine A mixture of 30.1 g of iron powder, 4.5 g of ammonium chloride, 930 ml of dioxane, and 400 ml of water was heated on a steam bath with stirring. To the mixture were added 50 g cf the nitro compound obtained in above step 3-(1) and the mixture was refluxed for 1.5 hours. Then, insoluble matter was filtrated away and after concentrating the filtrate under reduced pressure, water was added thereto. Crystals thus formed were collected by filtration and washed with 300 ml of isopropanol to provide 44 g of the desired product.

3-(3) Synthesis of Compound (2)

In 10.5 ml of N,N-dimethylacetamide were dissolved 19.0 g of the amino compound obtained in above step 3-(2) and the 16.2 g of urethane compound obtained in above step 2-(3) and then 18.3 ml of N-methylmorpholine were added thereto. After stirring the mixture for 7 hours at 60° C., the reaction mixture was cooled to room temperature and poured into 1 liter of diluted hydrochloric acid. Crystals thus formed were collected by filtration and washed with water to provide 13.0 g of Compound (2) having a melting point of from 153° C. to 158° C. (decompd.).

Now, the compound represented by general formula (II) described above is explained in detail.

$A_1$ and $A_2$ in formula (II) both are a hydrogen atom or one of them is a hydrogen atom and the other is an alkylsulfonyl group having not more than 20 carbon atoms, an arylsulfonyl group (preferably a phenylsulfonyl group or a phenylsulfonyl group substituted so that the sum of the Hammet's substituent constants becomes at least ⊖0.5), an acyl group (preferably a benzoyl group or a substituted benzoyl group so that the sum of the Hammett's substitution constants becomes at least ⊖0.5), or a straight chain, branched, or cyclic substituted or unsubstituted aliphatic acyl group wherein the substituent can be a halogen atom, an ether group, a sulfonamido group, a carbonamido group, a hydroxy group, a carboxy group, and a sulfonic acid group). $A_1$ and $A_2$ are most preferably a hydrogen atom.

G and $R_1$ in formula (II) are as follows.

When G is a carbonyl group, $R_1$ is preferably a hydrogen atom, an alkyl group (e.g., a methyl group, a trifluoromethyl group, a 3-hydroxypropyl group, or a 3-methanesulfonamidopropyl group), an aralkyl group (e.g., an o-hydroxybenzyl group), or an aryl group (e.g., a phenyl group, a 3,5-dichlorophenyl group, an o-methanesulfonamidophenyl group, or a 4-methanesulfonylphenyl group), and is more preferably a hydrogen atom.

When G is a sulfonyl group, $R_1$ is preferably an alkyl group (e.g., a methyl group), an aralkyl group (e.g., an o-hydroxyphenylmethyl group), an aryl group (e.g., a phenyl group), or a substituted amino group (e.g., a dimethylamino group).

When G is a carboxyl group, $R_1$ is preferably a cyanobenzyl group or a methylthiobenzyl group.

When G is a phosphoryl group, $R_1$ is preferably a methoxy group, an ethoxy group, a butoxy group, a phenoxy group, or a phenyl group, and more preferably a phenoxy group.

When G is an N-substituted or unsubstituted iminomethylene group, $R_1$ is a methyl group, an ethyl group, or substituted or unsubstituted phenyl group.

As the substituent for $R_1$, there are, for example, an alkyl group, an aralkyl group, an alkoxy group, an aryl group, a substituted amino group, an acylamino group, a sulfonylamino group, a ureido group, a urethane group, an aryloxy group, a sulfamoyl group, a carbamoyl group, an alkylthio group, an arylthio group, a sulfonyl group, a sulfinyl group, a hydroxyl group, a halogen atom, a cyano group, a carboxy group, an acyloxy group, an acyl group, an alkyloxycarbonyl group, an aryloxycarbonyl group, an alkenyl group, an alkinyl group, and a nitro group.

Also, these groups may combine with each other to form a ring.

In this case, G is most preferably a carbonyl group.

Examples of the arylene group represented by $L_1$ are a phenylene group and a naphthylene group and these groups may be substituted with an alkyl group, an aralkyl group, an alkoxy group, an aryl group, an aryloxy group, an alkenyl group, an alkylthio group, an arylthio group, a sulfonyl group, a sulfinyl group, a halogen atom, a cyano group, an acyl group, or a nitro group, for example.

The divalent linkage group represented by $L_2$ is an atom or an atomic group including at least one of C, N, S, and O and usually comprises an alkylene group, an alkenylene group, an alkynylene group, an arylene group, —O—, —S—, —NH—, —N=, —CO—, —SO_2—, etc., (these groups may be substituted) singly or as a combination thereof.

Examples of the divalent linkage group are

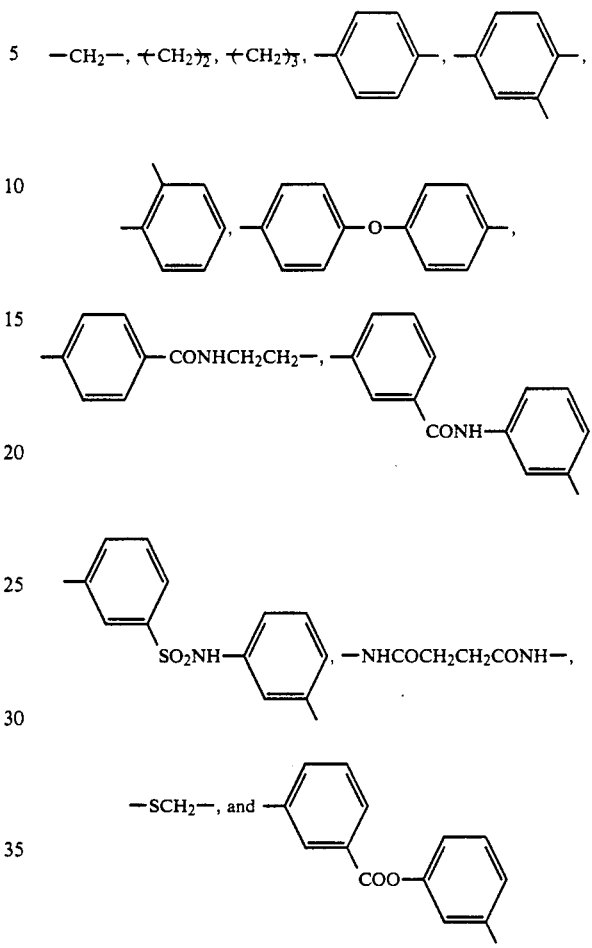

These groups may be further substituted by a substituent as described above as the substituent for $R_1$.

Practical examples of the adsorption accelerating group for silver halide represented by $X_1$ are cyclic thioamide groups such as 4-thiazoline-2-thione, 4-imidazoline-2-thione, 2-thiohydantoin, rhodanine, thiobarbituric acid, 1,2,4-triazoline-3-thione, 1,3,4-oxazoline-2-thione, benzimidazoline-2-thione, benzoxazoline-2-thione, benzothiazoline-2-thione, thiotriazine, 1,3-imidazoline-2-thione; an aliphatic mercapto group; an aromatic mercapto group; a heterocyclic mercapto group (when the atom adjacent to the carbon atom bonded to —SH group is a nitrogen atom, the heterocyclic mercapto group has the same meaning as the cyclic thioamide group which is in a tautomeric relation therewith); a group having a disulfide bond; and 5-membered or 6-membered nitrogen-containing heterocyclic groups composed of a combination of nitrogen, oxygen, sulfur and carbon, such as benzotriazole, triazole, tetrazole, indazole, benzimidazole, imidazole, benzothiazole, thiazole, thiozoline, benzoxazole, oxazole, oxazoline, thiadiazole, oxathiazole, triazine, and azaindene.

They may be further substituted by a substituent as illustrated above as the substituent for $R_1$.

$X_1$ is preferably a 3-mercapto-1,2,4-triazole group, a 2-mercapto-1,3-imidazole group, a 2-mercapto-1, 3,4-oxadiazole, a 2-mercaptobenzimidazole, or a benzotriazole.

Also, preferred compounds of the compounds shown by formula (II) are represented by following formula (II').

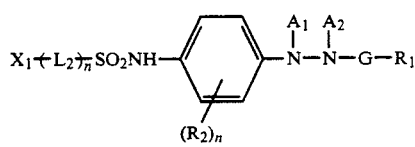

wherein $R_2$ represents the substituent as illustrated above as the substituent for $R_1$ in formula (II) and $R_1$, G, $A_1$, $A_2$, $L_2$, $X_1$, and m have the same meaning as described for formula (II) and n represents 0, 1 or 2.

Specific examples of compounds represented by formula (II) are illustrated below.

Compound-201

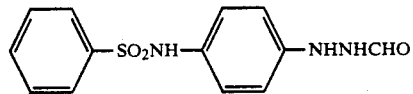

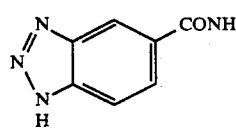

Compound-202

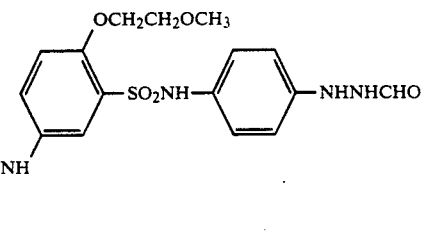

Compound-203

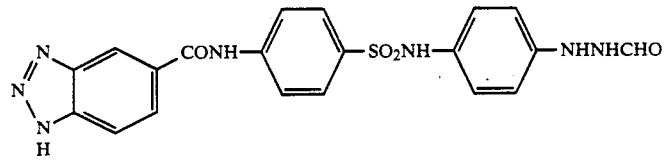

Compound-204

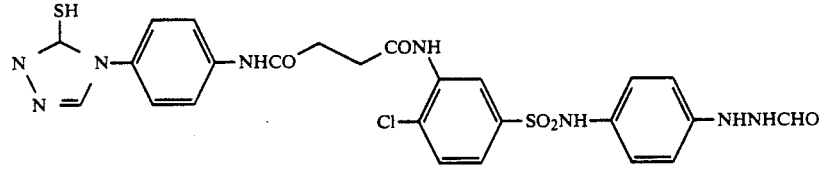

Compound-205

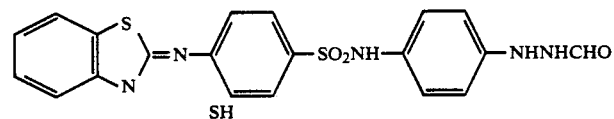

Compound-206

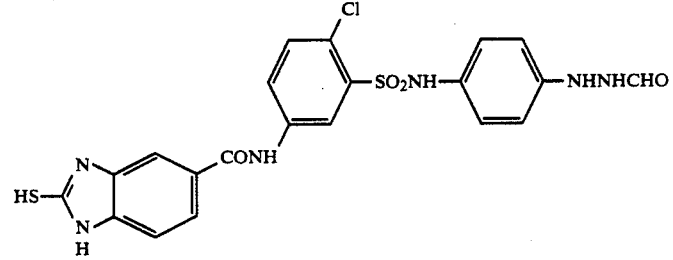

Compound-207

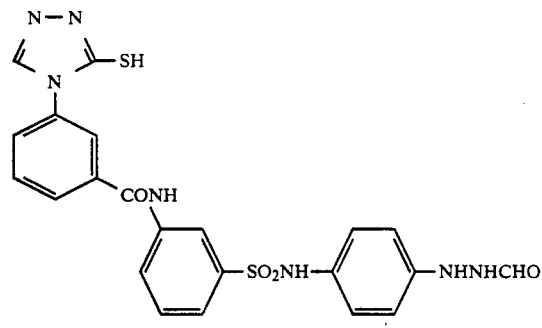
Compound-208
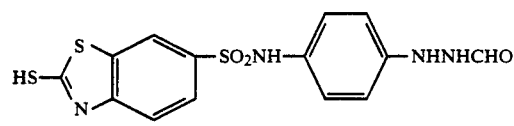
Compound-209
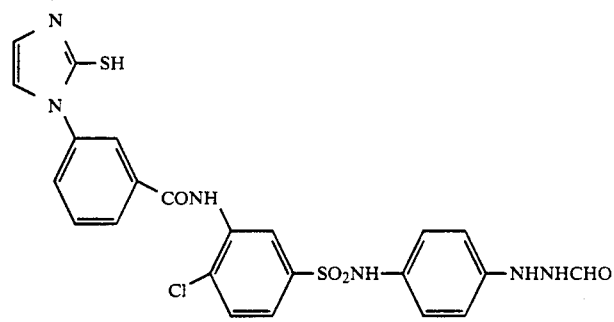
Compound-210
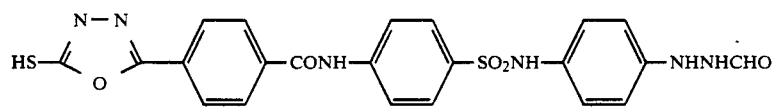
Compound-211
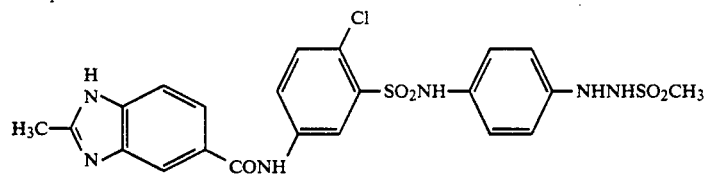
Compound-212
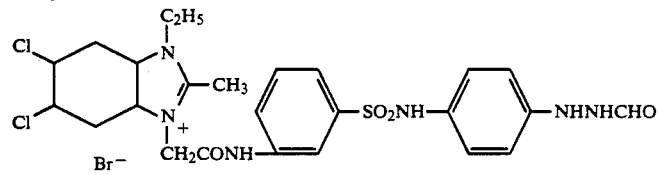
Compound-213
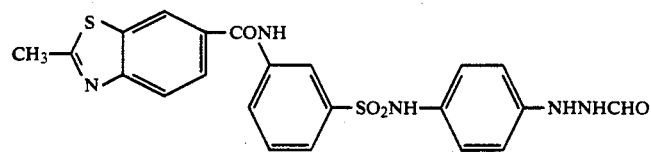
Compound-214

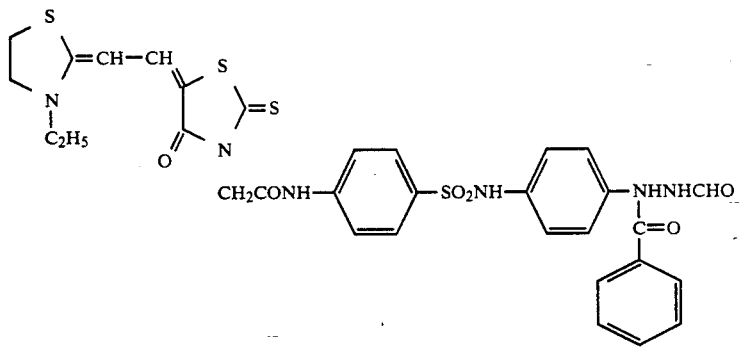
Compound-215
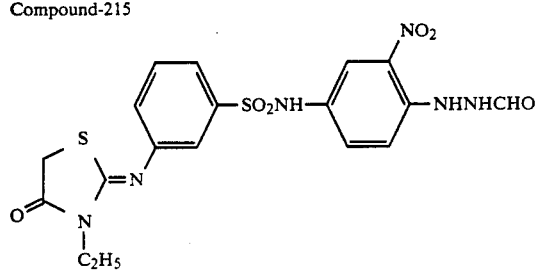
Compound-216
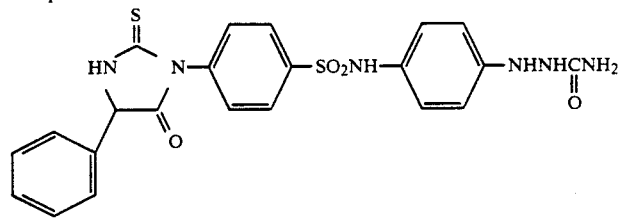
Compound-217
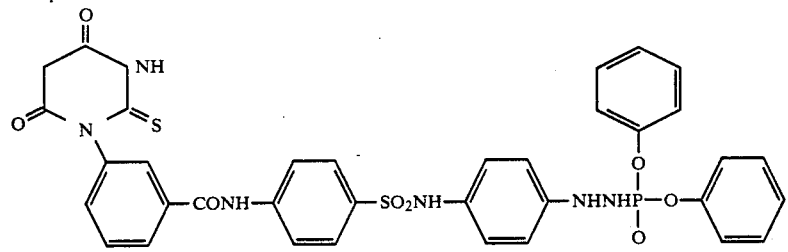
Compound-218
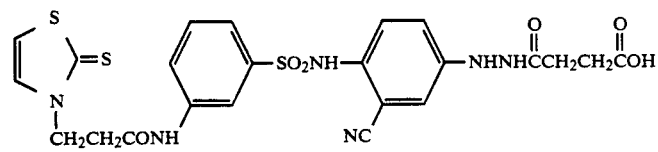
Compound-219
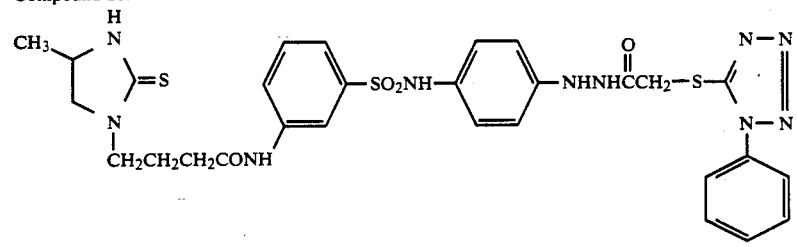
Compound-220

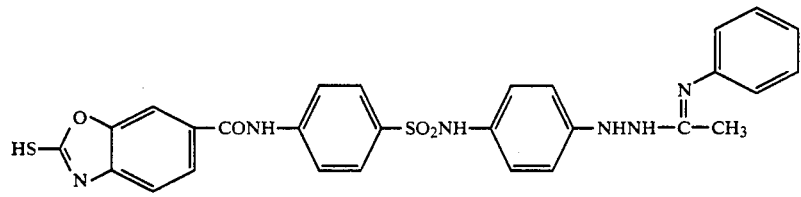
Compound-221
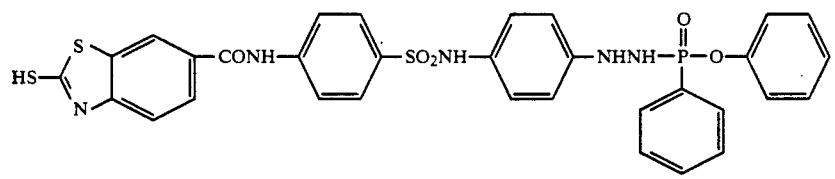
Compound-222
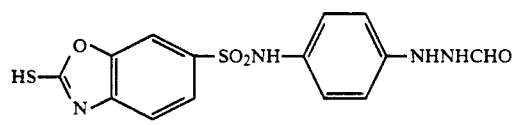
Compound-223
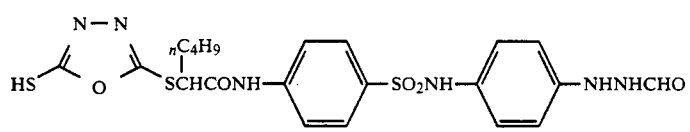
Compound-224
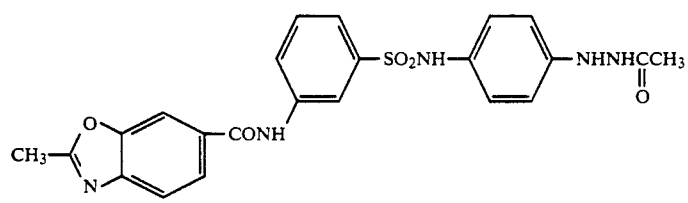
Compound-225
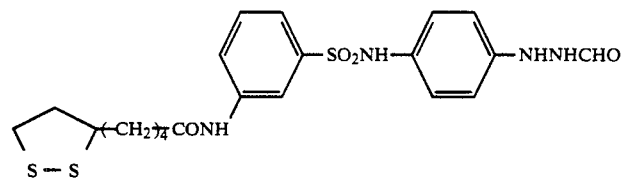
Compound-226
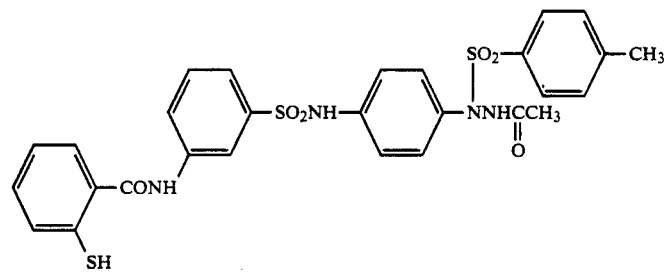
Compound-227

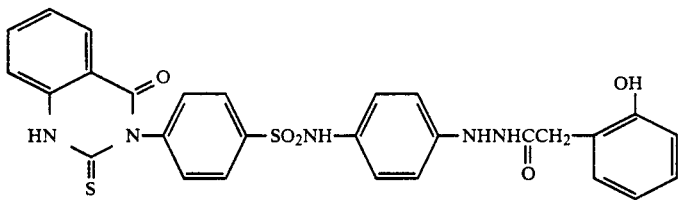
Compound-228
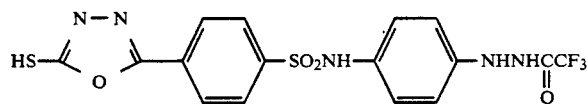
Compound-229
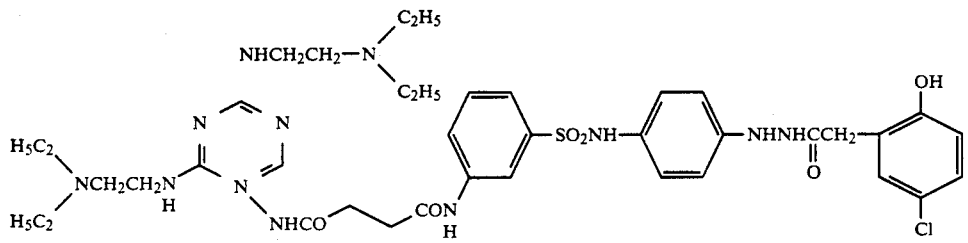
Compound-230
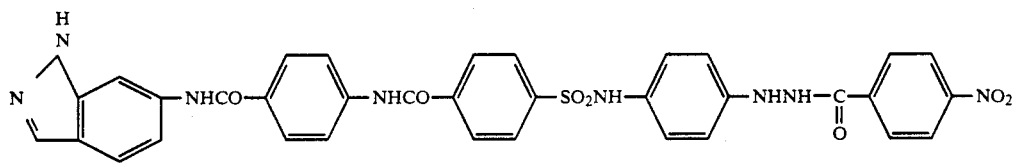
Compound-231
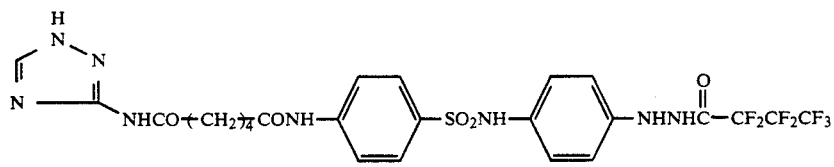
Compound-232
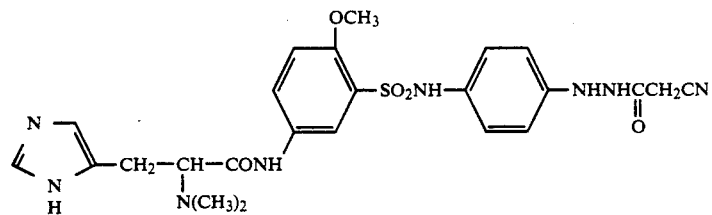
Compound-233
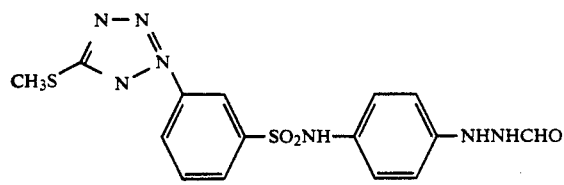
Compound-234

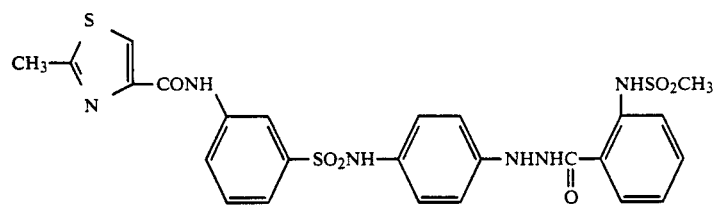
Compound-235
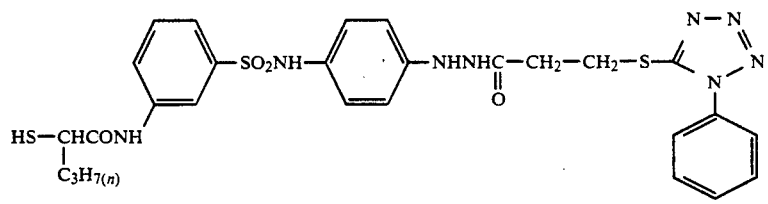
Compound-236
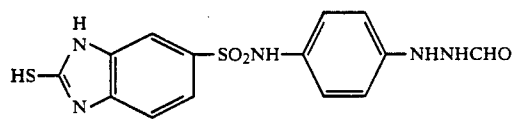
Compound-237
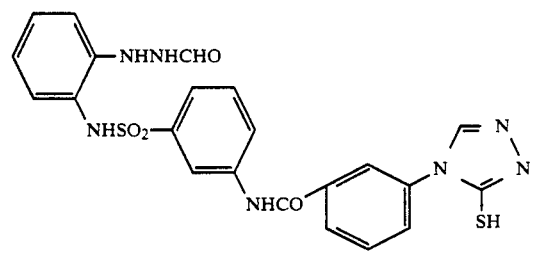
Compound-238
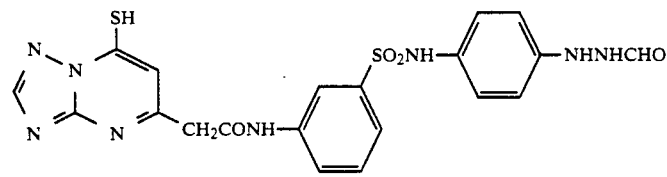
Compound-239
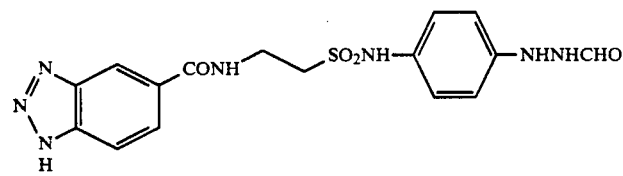
Compound-240
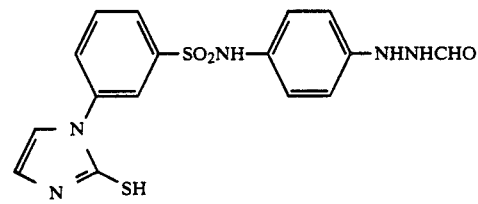
Compound-241

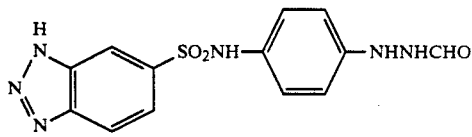

Compound-242

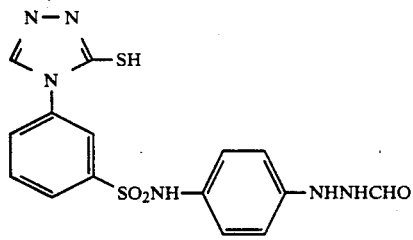

Compound-243

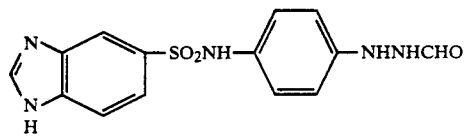

The compound represented by formula (II) can be synthesized generally as follows.

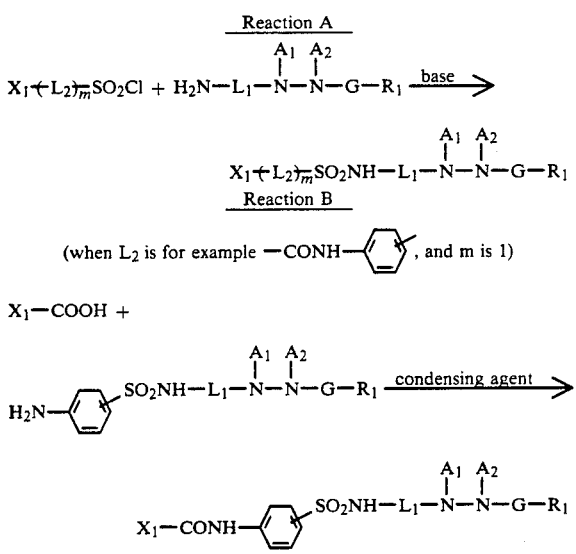

For these reactions, a solvent such as acetonitrile, tetrahydrofuran, dioxane, methylene chloride, chloroform, dimethylformamide, dimethylacetamide, etc., can be used.

As the base for reaction A, triethylamine, N-ethylpiperidine, N-methylmorpholine, pyridine, etc., can be used. As the condensing agent for reaction B, dicyclohexylcarbodiimide, carbonylimidazole, etc., can be used. In reaction B, a catalyst such as N,N-dimethylaminopyridine, pyrrolidinopyridine, N-hydroxybenzotriazole, etc., and the aforesaid base can be used for the improvement of the yield and shortening of the reaction time.

Then, typical synthesis examples for the compounds represented by formula (II) are illustrated.

Synthesis Example 4 Synthesis of Compound 201

4-(1) Synthesis of 2-[4-(3-nitrobenzenesulfonamido)-phenyl]-1-formylhydrazine

In 1 liter of N,N-dimethylacetamide, 880 ml of acetonitrile, and 285 g of triethylamine were dissolved 426 g of 2-(4-aminophenyl)-1-formylhydrazine in a nitrogen gas atmosphere, and after cooling to solution to $-5°$ C., 625 g of methanenitrobenzenesulfonyl chloride was gradually added thereto while cooling with stirring so that the liquid temperature was not over $-5°$ C. After further stirring the mixture for 1.5 hours at a temperature below $-5°$ C., the temperature was raised to room temperature and the reaction mixture was extracted with 12 liters of ethyl acetate and 12 liters of a saturated aqueous sodium chloride solution. The organic layer formed was collected and after concentrating it to 6 liters, 3 liters of n-hexane was added thereto followed by stirring for 30 minutes at room temperature. Crystals thus formed were collected by filtration and washed with 500 ml of ethyl acetate to provide 680 g of the desired product having a melting point of from 191° C. to 193° C.

4-(2) Synthesis of 2-[4-(3-aminobenzenesulfonamide)-phenyl]-1-formylpydrazine

A mixture of 680 g of iron powder, 68 g of ammonium chloride, 6.5 liters of isopropanol, and 2.2 liters of water was heated on a steam bath with stirring. To the mixture were added 680 g of the nitro compound obtained in above step 4-(1) and the mixture was refluxed for 1.5 hours. Then, insoluble matter was filtered away and after concentrating the filtrate under reduced pressure, water was added thereto. Crystals thus formed were collected by filtration and washed with isopropanol to provide 535 g of the desired product having a melting point of from 155° C. to 156° C.

4-(3) Synthesis of Compound 201

In 50 ml of dimethylformamide were dissolved 8.1 g of 5-carboxybenzotriazole and 15.3 g of the amino compound obtained in above step 4-(2) and while stirring the solution at 0° C. in a nitrogen gas atmosphere, 5 ml of dimethylformamide solution containing 10.3 g of dicyclohexylcarbodiimide were added dropwise to the solution over a period of 15 minutes. After stirring the mixture for one hour, the mixture was further stirred for 2 hours at 25° C. Then, dicyclohexylurea formed was removed by filtration and the filtrate thus obtained was added to 1.5 liters of ice water. Crude crystals thus deposited were collected by filtration and dispersed in 100 ml of isopropanol for 15 minutes under heating. The reaction mixture was cooled to room temperature and filtered to provide 12.1 g of desired Compound 201 having a melting point of from 196° C. to 199° C. (decompd.) with the yield of 54%.

Synthesis Example 5 Synthesis of Compound 206

5-(1) Synthesis of 2-[4-(2-chloro-5-nitrobenzenesulfonamido)phenyl]-1-formylhydrazine In 90 ml of N,N-dimethylacetamide, 76 ml of acetonitrile, and 19 ml of pyridine were dissolved 35.4 g of 2-(4-aminophenyl)-1-formylhydrazine in a nitrogen gas atmosphere and after cooling the solution to −5° C., 59:9 g of 2-chloro-5-nitrobenzenesulfonyl chloride was gradually added thereto while cooling with stirring so that the liquid temperature was not over −5° C. After further stirring the mixture for 1.5 hours at a temperature below −5° C., the temperature thereof was raised to room temperature and the reaction mixture was poured into 1 liter of a saturated aqueous sodium chloride solution. Crystals formed were collected by filtration and washed with water to provide 63 g of the desired product.

5-(2) Synthesis of 2-[4-(5-amino-2-chlorobenzenesulfonamido)phenyl]-1-formylhydrazone A mixture of 30.1 g of iron powder, 4.5 g of ammonium chloride, 930 ml of dioxane, and 400 ml of water was heated on a steam bath with stirring. To the mixture were added 50 g of the nitro compound obtained in above step 5-(1) and the mixture was refluxed for 1.5 hours. Then, insoluble matter was filtered off and after concentrating the filtrate under reduced pressure, the reaction mixture was extracted with ethyl acetate and a saturated aqueous sodium chloride solution. The organic layer formed was concentrated under reduced pressure to provide 43 g of the desired product as an oily product.

5-(3) Synthesis of Compound 206

By following the same procedure as in Synthesis Example 4 using 19.4 g of 5-carboxy-2-mercaptoimidazole and 34.1 g of the amino compound obtained in above step 5-(2), 31.5 g of Compound 206 was obtained with a yield of 61%. The melting point thereof was 185° C. to 188° C. (decompd.).

Synthesis Example 6 Synthesis of Compound 209

6-(1) Synthesis of 2-[4-(4-chloro-3-nitrobenzenesulfonamido)phenyl]-1-formylhydrazine In 90 ml of N,N-dimethylacetamide, 76 ml of acetonitrile, and 17 ml of pyridine were dissolved 35.4 g of 2-(4-aminophenyl)-1-formylhydrazine in a nitrogen gas atmosphere and after cooling the solution to −5° C., 59.9 g of 4-chloro-3-nitrobenzenesulfonyl chloride were gradually added to the solution while cooling with stirring so that the liquid temperature was not over −5° C. After further stirring the mixture for 1.5 hours at temperature below −5° C., the temperature was raised to room temperature and the reaciton mixture was poured into 1 liter of a saturated aqueous solid chloride solution. Crystals formed were collected by filtration and washed with water to provide 67.5 g of the desired product.

6-(2) Synthesis of 2-[4-(3-amino-4-chlorobenzenesulfonamido)phenyl]-1-formylhydrazine A mixture of 30.1 g of iron powder, 4.5 g of ammonium chloride, 930 ml of dioxane, and 400 ml of water was heated on a steam bath with stirring. To the mixture were added 50 g of the nitro compound obtained in above step 6-(1) and the mixture was further refluxed for 1.5 hours. Then, insoluble matter was filtered off and after concentrating the filtrate under reduced pressure, water was added to the residue. Crystals thus formed were collected by filtration and washed with 300 ml of isopropanol to provide 44 g of the desired product.

6-(3) Synthesis of Compound 209

By following the same procedure as Synthesis Example 4 using 22.0 g of 1-(4-carboxyphenyl)-2-mercaptoimidazole and 34.1 g of the amino compound obtained in above step 6-(2), 34.8 g of Compound 209 was obtained with a yield of 64%. The melting point was 201° C. to 205° C. (decompd.).

Synthesis Example 7 Synthesis of Compound 213

To 1.93 g of 2-methyl-6-carboxybenzothiazole were added 25 ml of N,N-dimethylformamide and 2.55 ml of pyridine and the mixture obtained was cooled to −15° C. Then, 1.76 g of benzenesulfonyl chloride were added dropwise to the mixture while keeping the liquid temperature below −5° C. and the resultant mixture was stirred for 10 minutes. After cooling the mixture to −15° C., a solution of 3.06 g of the amino compound obtained in above step 4-(2) dissolved in 10 ml of N,N-dimethylformamide was added dropwise to the mixture while cooling so that the temperature of the reaction mixture was not over −5° C. Then, after stirring the mixture for 20 minutes, the mixture was further stirred for one hour at room temperature. Then, 50 ml of acetonitrile were added thereto. Crystals thus formed were collected by filtration and washed with acetonitrile. The crystals obtained were dissolved in 100 ml of methanol and activated carbon was added to the solution. After removing insoluble matters by filtration, 150 ml of acetonitrile was added to the filtrate and crystals formed were collected by filtration, washed with acetonitrile, and then dried to provide 2.0 g of the desired compound having a melting point of 189° C. (decompd.) with a yield of 42%.

Synthesis Example 8 Synthesis of Compound 225

A solution comprising of 20 ml of N,N-dimethylacetamide, 2 g of triethylamine, and 4.1 g of D,L-lipoic acid was cooled to −15° C. and then 1.67 g of ethyl chloroformate were added dropwise to the solution. After stirring the mixture for 15 minutes, a solution of 6.1 g of the amino compound obtained in above step 4-(2) dissolved in 10 ml of N,N-dimethyl-acetamide was added dropwise to the mixture over a period of 30 minutes while cooling so that the liquid temperature was not over −7° C. After stirring the mixture for 30 minutes at −15° C., the reaction mixture was stirred for 2 hours and 45 minutes at room temperature and then poured into 200 ml of an aqueous solution of 2% sodium hydrogencarbonate. Crystals thus formed were collected by filtration and recrystallized from a mixture of 50 ml of acetonitrile, 30 ml of ether, and 10 ml of dioxane. Crystals formed were collected by filtration, washed with ether, and dried to provide 2.2 g of Compound 225 having a melting point of from 172° C. to 175° C. (decompd.) with a yield of 22%.

Synthesis 9 Synthesis of Compound 242

9-(1) Synthesis of 3-(2-mercapto-1,3,4-triazoyl)-phenylsulfonyl chloride

To a solution of 10 g of sodium 3-(2-mercapto-1,3,4-triazoyl)phenylsulfonate in 7 ml of thionyl chloride were added dropwise 10 ml of N,N-dimethylformamide with stirring under ice-cooling and after gradually raising the temperature to room temperature, the mixture was stirred for 2 hours.

Then, excess thionyl chloride was distilled off from the reaction mixture under reduced pressure, ice water was added to the residue obtained, and the product was extracted twice with chloroform. The extract was dried by anhydrous magnesium sulfate and then concentrated under reduced pressure to provide 3.8 g of 3-(5-mercapto-1,3,4-triazoyl)phenylsulfonyl chloride as a colorless oily product with a yield of 38%.

9-(2) Synthesis of Compound 242

To 10 ml of an N,N-dimethylformamide solution of 2.2 g of 1-formyl-2-(4-aminophenyl)hydrazine were added 1.4 ml of pyridine under ice cooling in a nitrogen gas atmosphere. After further adding dropwise 5 ml of an acetonitrile solution of 4.1 g of 3-(2-mercapto-1,3,4-triazoyl)phenylsulfonyl chloride, the resultant mixture was stirred for one hour under ice-cooling. Thr reaction mixture was poured into a mixture of 100 ml of water and 3 ml of hydrochloric acid. Crystals thus formed were collected by filtration and recrystallized from isopropyl alcohol to provide 2.5 g of Compound 242 having a melting point of from 162° C. to 165° C. (decompd.) with a yield of 65%.

The compound represented by formula (III) described above is now explained in detail.

$A_1$ and $A_2$ in formula (III) both are a hydrogen atom or one of them is a hydrogen atom and the other is an alkylsulfonyl group having not more than 20 carbon atoms, an arylsulfonyl group (preferably a phenylsulfonyl group or a phenylsulfonyl group substituted so that the sum of the Hammett's substituent constants becomes at least $\ominus 0.5$), an acyl group having nor more than 20 carbon atoms (preferably a benzoyl group or a substituted benzoyl group that the sum of the Hammett's substituent constants becomes at least $\ominus 0.5$), or a straight chain, branched, or cyclic unsubstituted or substituted aliphatic acyl group (examples of the substituent are a halogen atom, an ether group, a sulfonamido group, a carbonamido group, a hydroxy group, a carboxy group, and a sulfonic acid group).

The sulfinic acid residue represented by $A_1$ or $A_2$ is described in U.S. Pat. No. 4,478,928;

$A_1$ and $A_2$ are most preferably a hydrogen atom.

G and $R_1$ in formula (III) are as follows.

When G is a carbonyl group, $R_1$ is preferably a hydrogen atom, an alkyl group (e.g., a methyl group, a trifluoromethyl group, a 3-hydroxypropyl group, or a 3-methanesulfonamidopropyl group), or an aryl group (e.g., a phenyl group, a 3,5-dichlorophenyl group, an o-methanesulfonamidophenyl group, or a 4-methanesulfonylphenyl group), and is more preferably a hydrogen atom.

When G is a sulfonyl group, $R_1$ is preferably an alkyl group (e.g., a methyl group), an aralkyl group (e.g., a phenyl group), or a substituted amino group (e.g., a dimethylamino group).

When G is a sulfoxy group, $R_1$ is preferably a cyanobenzyl group or a methylthiobenzyl group.

When G is a phosphoryl group, $R_1$ is preferably a methoxy group, an ethoxy group, a butoxy group, a phenoxy group, or a phenyl group, and more preferably a phenoxy group.

When G is an N-substituted or unsubstituted iminomethylene group, $R_1$ is a methyl group, an ethyl group, or a substituted or unsubstituted phenyl group.

Examples of the substituent for $R_1$ are an alkyl group, an aralkyl group, an alkoxy group, an aryl group, a substituted amino group, an acylamino group, a sulfonylamino group, a ureido group, a urethane group, an aryloxy group, a sulfamoyl group, a carbamoyl group, an aryl group, an alkylthio group, an arylthio group, a sulfonyl group, a sulfinyl group, a hydroxyl group, a halogen atom, a cyano group, a sulfo group, a carboxyl group, an acyloxy group, an acyl group, an alkyloxycarbonyl group, an aryloxycarbonyl group, an alkenyl group, an alkinyl group, an alkinyl group, and a nitro group. These groups may be further substituted.

Also, these groups may combine with each other to form a ring.

In this case, G is most preferably a carbonyl group.

Examples of the arylene group represented by $L_1$ are a phenylene group and a naphthylene group and they may be substituted by a substituent exemplified above for $R_1$. $L_1$ is more preferably a phenylene group.

The divalent linkage group represented by $L_2$ is an atom or an atomic group including at least one of C, N, S, and O and is usually comprised of an alkylene group, an alkenylene group, an alkinylene group, an arylene group, —O—, —S—, —NH—, —N=, —CO—, —SO$_2$—, etc., (these groups may be substituted) singly or as a combination thereof.

Examples of the divalent linkage group are

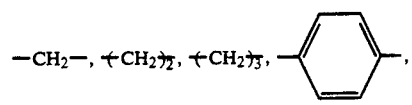

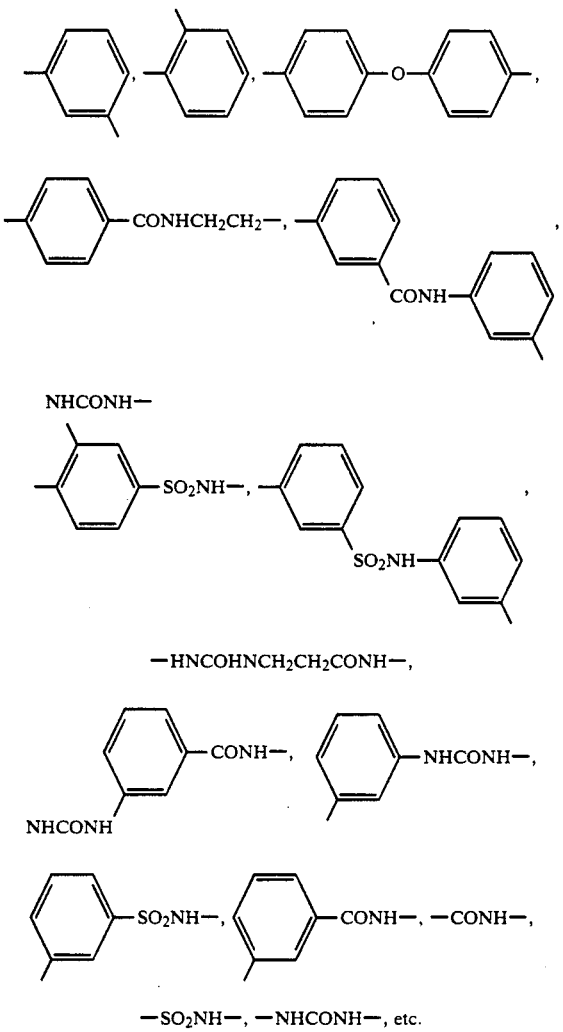

—SO₂NH—, —NHCONH—, etc.

Preferred examples of the adsorption accelerating group for silver halide represented by $X_1$ are a thioamide group, a mercapto group, a group having a disulfide bond, or a 5- or 6-membered nitrogen-containing heterocyclic group.

The thioamide adsorption accelerating group represented by $X_1$ is a divalent group shown by

—C-amino-, which may be a part of ring structure or an acylic thioamide group.

Useful thioamide adsorption accelerating groups are described in, for example, U.S. Pat. Nos. 4,030,925, 4,031,127, 4,080,207, 4,245,037, 4,255,511, 4,266,013, and 4,276,364, Rearch Disclosure, Vol. 151, No. 15162 (November, 1976) and R.D., Vol. 176, No. 17626 (December, 1978).

Examples of the acyclic thioamide group include a thioureido group, a thiourethane group, and a dithiocarbamic acid ester group. Examples of the cyclic thioamide group are 4-thiazoline-2-thione, 4-imidazoline-2-thione, 2-thiohydantoin, rhodanine, thiobarbituric acid, tetrazoline-5-thione, 1,2,4-triazoline-3-thione, 1,3,4-thiadiazoline-2-thione, 1,3,4-oxadiazoline-2-thione, benzimidazoline-2-thione, benzoxazoline-2-thione, and benzothiazoline-2-thione. They may be further substituted.

As the mercapto group represented by $X_2$, there are an aliphatic mercapto group, an aromatic mercapto group, and a heterocyclic mercapto group (when the atom adjacent to the carbon atom bonded to —SH group is a nitrogen atom, the mercapto group has the same meaning as a cyclic thioamide group which is in a tautomeric relation therewith and practical examples thereof are same as illustrated above).

As the 5- or 6-membered nitrogen-containing heterocyclic group represented by $X_1$ are 5- or 6-membered nitrogen-containing heterocyclic rings comprises a combination of nitrogen, oxygen, sulfur, and carbon. Preferred examples thereof are benzotriazole, triazole, tetrazole, indazole, benzimidazole, imidazole, benzothiazole, thiazole, benzoxazole, oxazole, thiadiazole, oxadiazole, and triazine. They may be further substituted by a substituent as illustrated above for $R_1$.

$X_1$ is preferably a cyclic thioamide group (e.g., a mercapto-substituted nitrogen-containing heterocyclic ring, such as a mercaptothiadiazole group, a 3-mercapto 1,2,4-triazole group, a 5-mercaptotetrazole group, a 2-mercapto-1,3,4-oxadiazole group, or a 2-mercaptobenzoxazole) or a nitrogen-containing heterocyclic group (e.g., a benzotriazole group, a benzimidazole group or an indazole group).

The substituent capable of being dissociated into an anion of pKa of at least 6 represented by $Y_1$ is preferably a substituent capable of being dissociated into an anion having pKa of from 8 to 13. A substituent which is hardly dissociated in a neutral or weakly acidic medium and is sufficiently dissociated in an alkaline aqueous solution (having preferably pH of 10.5 to 12.3) such as a developer can be used without any restriction.

Examples of such a substituent are a hydroxyl group, a group represented by $R_2SO_2NH$— or $R_3NHSO_2$— (wherein $R_2$ and $R_3$ each represents an alkyl group, an aryl group, or a heterocyclic group), a hydroxyimino group ($>C=N$—OH), an active methylene group and an active methine group (e.g., —CH₂COOC₂H₅,

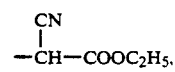
—CH—COOC₂H₅, etc.).

Also, the amino group of

wherein $R_4$ which may be the same or different, each represents a hydrogen atom, an alkyl group, an aryl group, or a heterocyclic group or $R_4$ and $R_5$ may combine with each other to form a ring) represented by $Y_1$ may be a primary, secondary or tertiary amine and has preferably at least 6.0 of pKa of the corresponding conjugate acid thereof.

Preferred compounds of the compounds represented by formula (III) are shown by following formula (III');

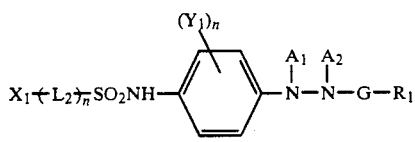
(III')
wherein $A_1$, $A_2$, G, $R_1$, $L_2$, $X_1$, $Y_1$, m and n have the same meaning as defined on formula (III).
Specific examples of the compound represented by formula (III) are illustrated below but the invention is not limited to these compounds.
Compound-301
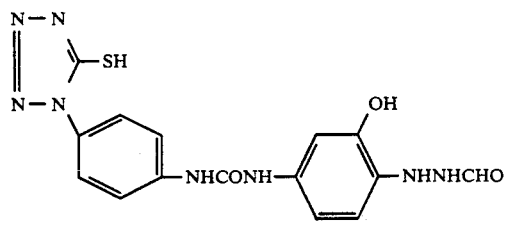
Compound-302
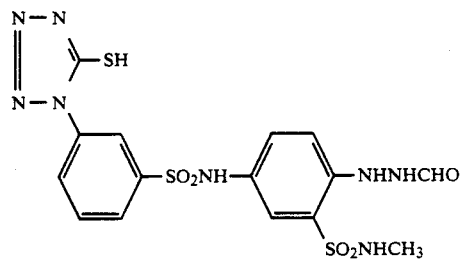
Compound-303
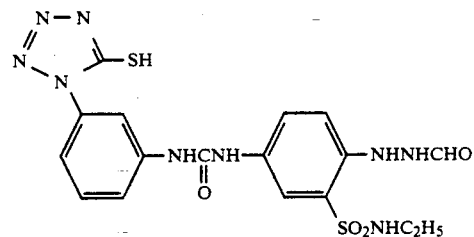
Compound-304
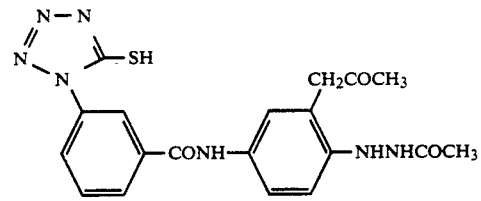
Compound-305
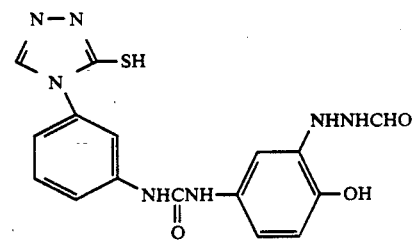
Compound-306

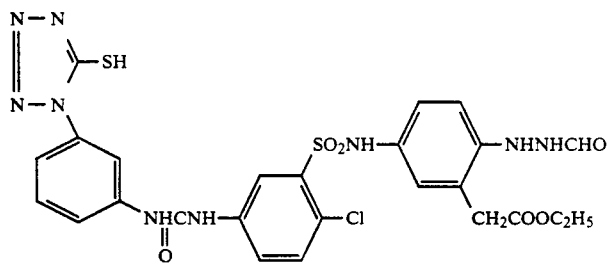
Compound-307
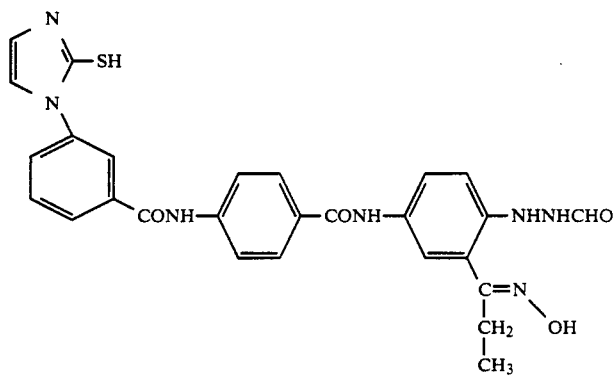
Compound-308
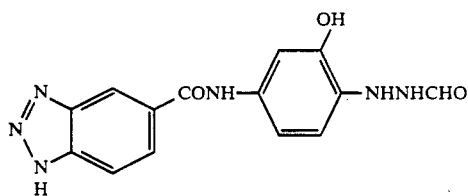
Compound-309
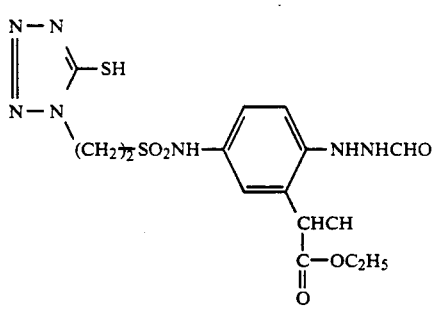
Compound-310
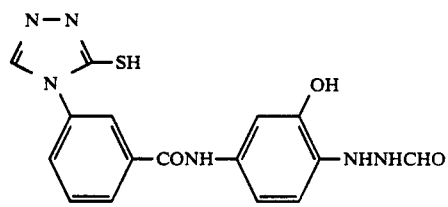
Compound-311

-continued
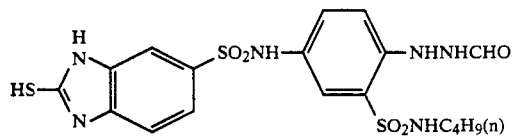
Compound-312
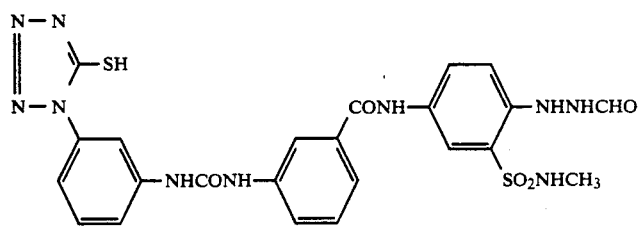
Compound-313
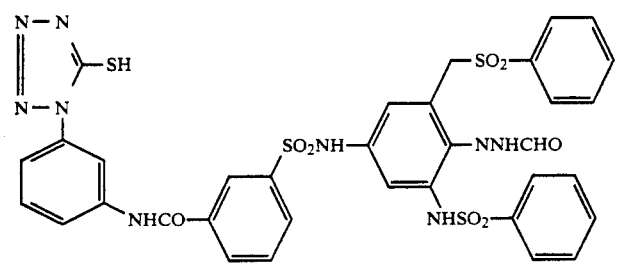
Compound-314
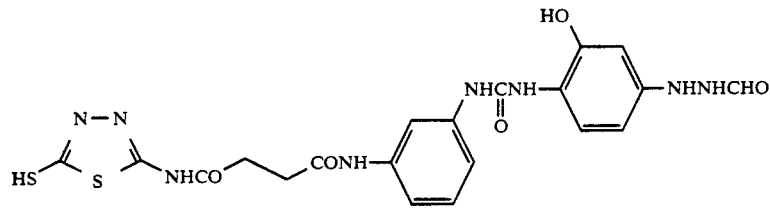
Compound-315
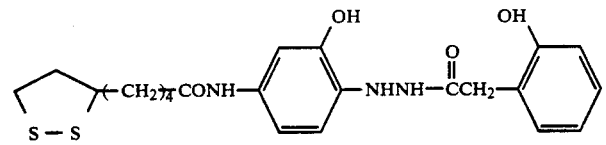
Compound-316
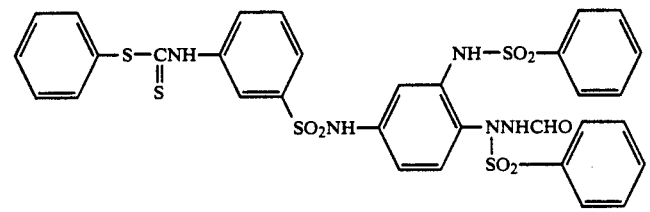
Compound-317

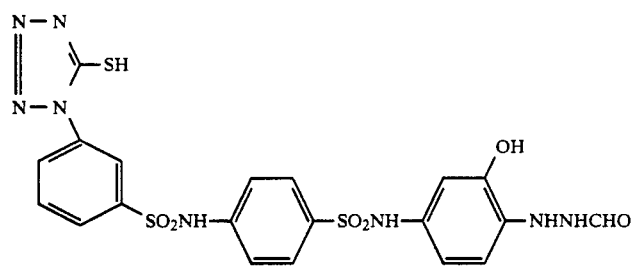
Compound-318
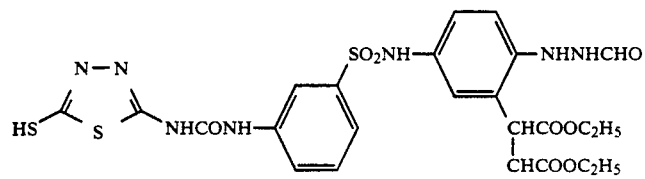
Compound-319
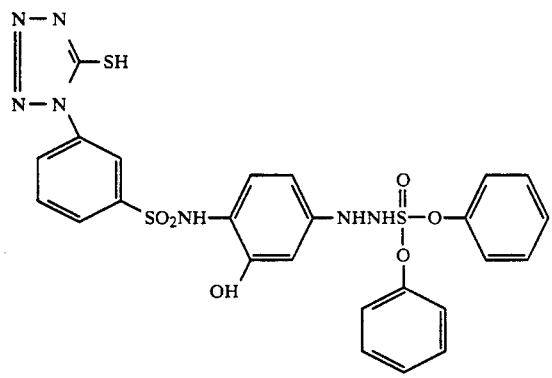
Compound-320
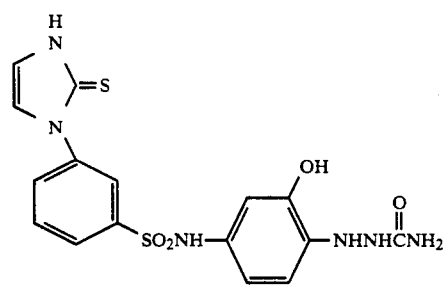
Compound-321
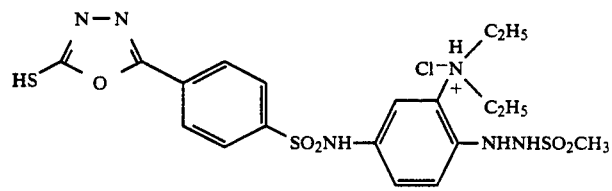
Compound-322

-continued
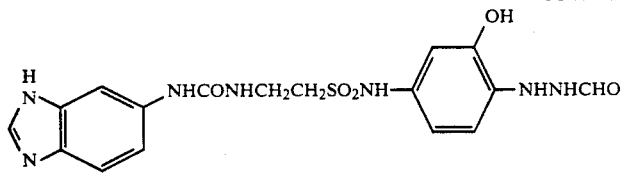
Compound-323
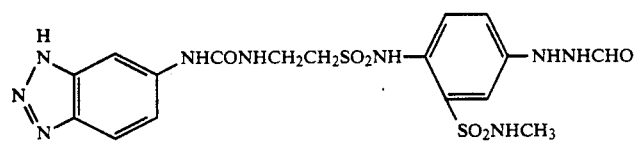
Compound-324
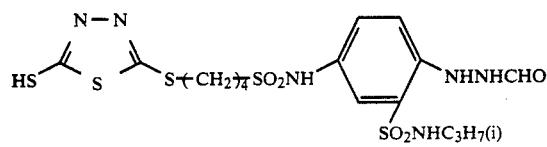
Compound-325
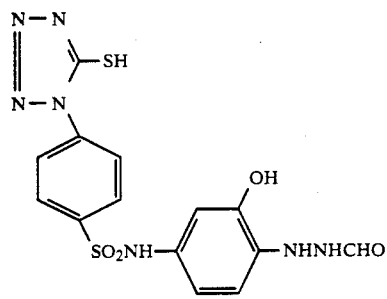
Compound-326
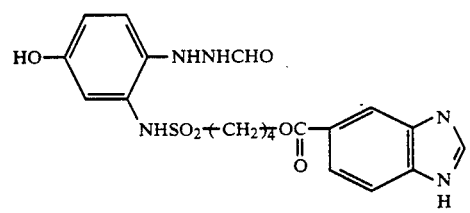
Compound-327
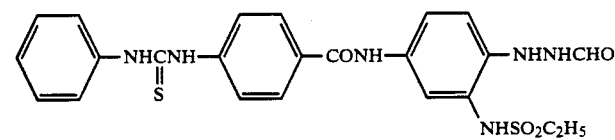
Compound-328
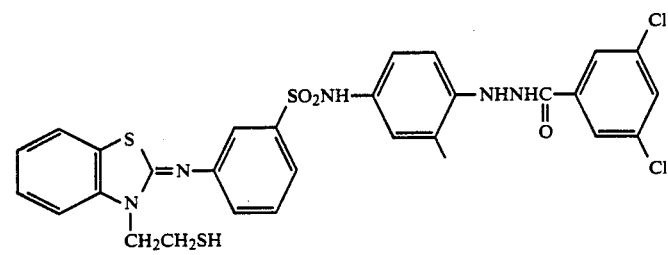

Compound-329
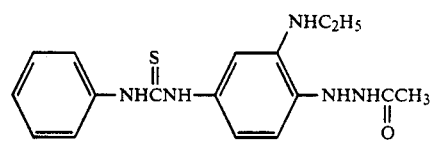
Compound-330
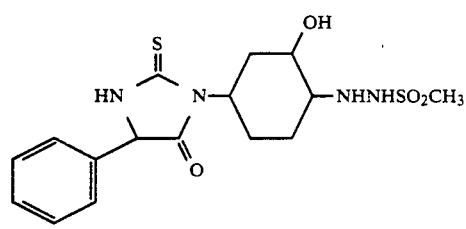
Compound-331
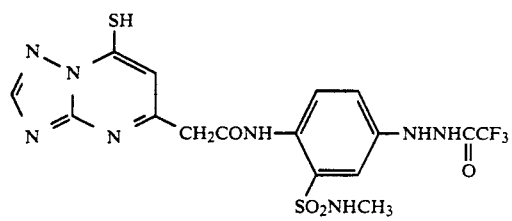
Compound-332
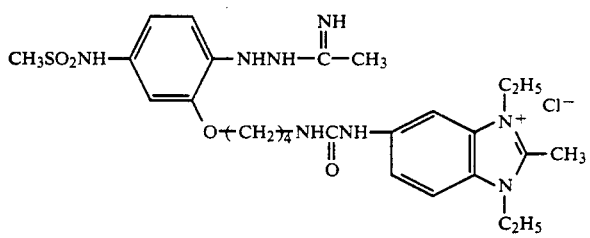
Compound-333
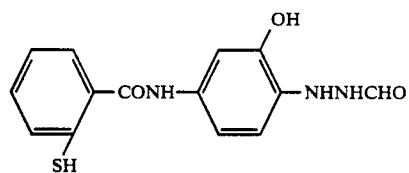
Compound-334
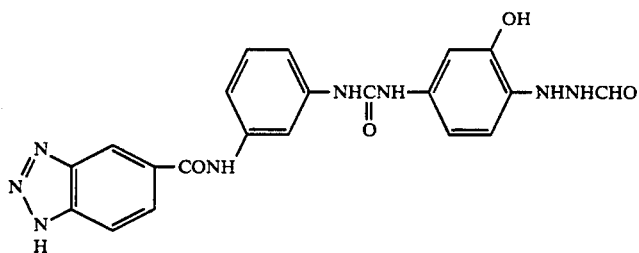
Compound-335

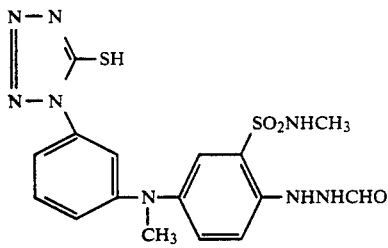

Compound-336

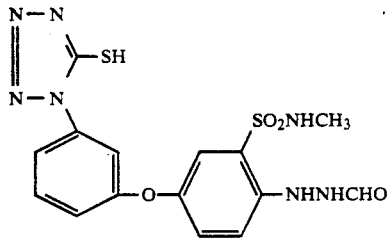

The compound shown by formula (III) described above can be synthesized generally as follows.

When $L_2$ is $-SO_2NH-$:

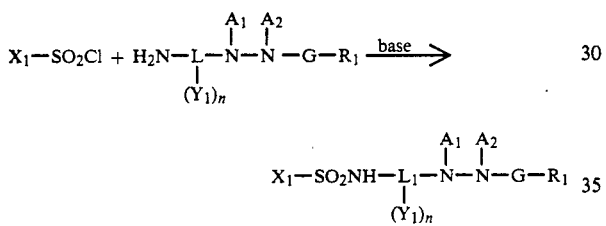

When $L_2$ is $-CONH-$:

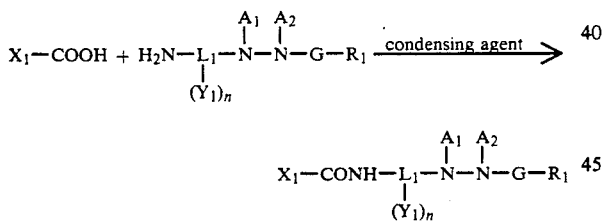

In these reactions, a solvent such as acetonitrile, tetrahydrofuran, dioxane, methylene chloride, chloroform, dimethylformamide, dimethylacetamide, etc., can be used. Also, as the base for reaction A, there are triethylamine, N-ethylpiperidine, N-methylmorpholine, pyridine, etc. As the condensing agent for reaction B, there are dicyclohexylcarbodiimide, carbonylimidazole, etc.

Also, in reaction B, the condensing agent may be used together with a catalyst such as N,N-dimethylaminopyridine, pyrrodinopyridine, N-hydroxybenzotriazole, etc., and/or the aforesaid base for improving the yield or shortening the reaction time.

Typical synthesis examples of the compounds represented by formula (III) are explained below.

Synthesis Example 10 Synthesis of Compound 301

10-(1) Synthesis of 2-(4-amino-2-hydroxyphenyl)-1-formylhydrazine

A mixture of 120 g of iron powder, 5 g of ammonium chloride, 2 liters of dioxane, and 800 ml of water was heated on a steam bath with stirring and after adding thereto 61 g of 2-(4-nitro-2-hydroxyphenyl)-1-formylhydrazine with stirring, the resultant mixture was refluxed for 40 minutes. Then, insoluble matters were distilled off the filtrate was concentrated under reduced pressure, and water was added to the residue. Crystals thus formed were collected by filtration and washed with acetonitrile to provide 40 g of the desired compound with a yield of 79%.

10-(2) Synthesis of 1-(3-phenoxycarbonylaminophenyl)-5-mercaptotetrazole

After dissolving 391 g of 1-(3-aminophenyl)- 5-mercaptotetrazole hydrochloride in 800 ml of N,N-dimethylformamide in a nitrogen gas atmosphere, the mixture was cooled to a temperature below 0° C. After adding thereto 302 ml of pyridine, 294 g of phenyl chloroformate were added dropwise to the s-lution while cooling with stirring so that the liquid temperature was not over 0° C. After further stirring the mixture for one hour at a temperature below 0° C., the reaction mixture was added dropwise to 5 liters of a saturated aqueous sodium chloride solution followed by stirring for 30 minutes. Crystals formed were collected by filtration and washed with 2 liters of water to provide 495 g of the desired compound with a yield of 93%.

10-(3) Synthesis of Compound 301

In 10 ml of acetonitrile were dissolved 1.7 g of the amino compound obtained in above step 10-(1) and 2.7 g of imidazole in a nitrogen gas atmosphere and after heating the solution to 65° C., a solution of 3.4 g of the urethane compound obtained in above step 10-(2) dissolved in 5 ml of N,N-dimethylacetamide was added dropwise to the solution followed by stirring for 1.5 hours at 65° C. The reaction mixture was cooled to 30° C. and extracted with 240 ml of ethyl acetate and 240 ml of water. The aqueous layer thus formed was collected and poured into a 0.5N diluted aqueous solution of hydrochloric acid. Crystals thus formed were collected by filtration and washed with water to provide 2.7 g of Compound 301 having a melting point of from 201° C. to 203° C. (decompd.) with a yield of 72%.

Synthesis Example 11 Synthesis of Compound 325

11-(1) Synthesis of 4-(5-mercaptotetrazoyl)-phenylsulfonyl chloride

To a solution of 10 g of sodium 4-(5-mercaptotetrazoyl)phenylsulfonate in 7 ml of thionyl chloride were added dropwise 10 ml of N,N-dimethylformamide with stirring under ice-cooling and after gradually raising the temperature to room temperature, the mixture was stirred for 2 hours. Then, excess thionyl chloride was distilled off from the reaction mixture under reduced pressure. The residue obtained was poured into ice water and extracted twice with chloroform. The extract was dried by anhydrous magnesium sulfate and concentrated under reduced pressure to provide 3.5 g of 4-(5-mercaptotetrazoyl)phenylsulfonyl chloride as a colorless oily product. The yield was 38%.

11-(2) Synthesis of Compound 325

To a solution of 2.4 g of the amino compound obtained in above step 10-(1) dissolved in 1.4 ml of N,N-dimethylformamide were added 1.4 ml of pyridine under ice-cooling in a nitrogen gas atmosphere. Then a solution of 3.5 g of 4-(5-mercaptotetrazoyl)phenylsulfonyl chloride obtained in above step 11-(1) dissolved in 5 ml of acetonitrile was added dropwise to the solution followed by stirring for one hour under ice cooling. The reaction mixture was poured into a solution comprising 100 ml of water and 3 ml of hydrochloric acid. Crystals thus formed were collected by filtration and recrystalized from isopropyl alcohol to provide 4.6 g of Compound 325 having a melting point of 186° C. (decompd.) with a yield of 79%.

Synthesis Example 12 Synthesis of Compound 308

In 20 ml of N,N-dimethylacetamide were dissolved 2.4 g of 5-phenoxycarbonylbenzotriazole and 1.7 g of the amino compound obtained in above step 10-(1) in a nitrogen gas atmosphere. After adding thereto 2.1 g of N-methylmorpholine, the mixture was stirred for 5 hours at room temperature. The reaction mixture was poured into 300 ml of an aqueous 0.1N hydrochloric acid solution and crystals thus formed were collected by filtration and washed with 500 ml of water to provide 2.1 g of Compound 308 having a melting point of 181° C. to 183° C. (decompd.) with a yield of 68%.

Synthesis Example 13 Synthesis of Compound 334

13-(1) Synthesis of 2-{2-hydroxy-4-}3-(3-nitrophenyl)-ureido{phenyl}-1-formylhydrazine In 200 ml of acetonitrile and 200 ml of N,N-dimethylformamide were dissolved 61.8 g of the amino compound obtained in above step 10-(1) and after cooling the solution to −5° C., a solution of 65.6 g of m-nitrophenyl isocyanate dissolved in 200 ml of acetonitrile was added dropwise to the solution while cooling with stirring so that the liquid temperature was not over −5° C. Furthermore, 300 ml of acetonitrile was added thereto followed by stirring for 3 hours at 0° C. Crystals thus formed were collected by filtration and washed with acetonitrile and then methanol. The crystals were dissolved in one liter of N,N-dimethylformamide. After filtering off insoluble matters, 3 liters of methanol were added to the filtrate, and the mixture was cooled to form crystals, which were collected by filtration and washed with acetonitrile and then methanol to provide 98.8 g of the desired product with a yield of 81%.

13-(2) Synthesis of 2-{2-hydroxy-4-}3-(3-aminophenyl)-ureido{phenyl}-1-formylhydrazine A mixture of 138 g of iron powder, 5 g of ammonium chloride, 2.45 liters of dioxane, and 985 ml of water was heated on a steam bath with stirring. To the mixture were added 99 g of the nitro compound obtained in above step 13-(1) and the resultant mixture was refluxed for 40 minutes. Then, insoluble matters were filtered off and after concentrating the filtrate under reduced pressure, water was added to the residue. Crystals thus formed were collected by filtration and washed with acetonitrile to provide 76 g of the desired product with a yield of 84%.

13-(3) Synthesis of Compound 334

In 20 ml of N,N-dimethylacetamide were dissolved 2.4 g of 5-phenoxycarbonylbenzotriazole and 1.7 g of the amino compound obtained in above step 13-(2) and after adding thereto 2.1 g of N-methylmorpholine, the mixture was stirred for 7 hours at room temperature. The reaction mixture was poured into 300 ml of an aqueous 0.1N hydrochloric acid solution and crystals formed were collected by filtration and washed with 500 ml of water to provide 1.4 g of Compound 334 having a melting point of 186° C. to 188° C. (decompd.) with a yield of 45%.

For incorporating at least one of the aforesaid compounds of this invention into a silver halide emulsion layer or a hydrophilic colloid layer, the compound is dissolved in water or an organic solvent miscible with water (if necessary, an alkali hydroxide or a tertiary amine may be added thereto to form a salt of the compound for dissolving it) and added to a hydrophilic colloid solution (e.g., a silver halide emulsion or an aqueous gelatin solution, etc.). In this case, if necessary, the pH of the mixture may be adjusted by adding an acid or alkali.

The compounds of this invention may be used singly or as a mixture thereof. The amount of the compounds added per mol of silver halide is preferably from $1 \times 10^{-5}$ mole to $5 \times 10^{-2}$ mole, more preferably from $2 \times 10^{-5}$ mole to $1 \times 10^{-2}$ mole. The amount may be suitably selected according to the nature of the silver halide emulsion to be combined.

When the compound represented by formula (I) described above is used in combination with a negative working silver halide emulsion, high contrast negative images can be formed. On the other hand, the compound of formula (I) can be used in combination with an internal latent image type silver halide emulsion. It is preferred, however, that the compound of formula (I) is utilized for forming high contrast negative images by using it in combination with a negative working silver halide emulsion.

In the case of high contrast negative images, the mean grain size of the silver halide grains is preferably fine (e.g., less than 0.7 μm), and more preferably less than 0.5 μm. There is no particular restriction on the grain size distribution of the emulsion, but a monodisperse silver halide emulsion is preferred. A monodisperse emulsion herein used means a silver halide emulsion containing silver halide grains at least 95% of which are within ±40% of the mean grain size by weight or grain number.

The silver halide grains for use in this invention may have a regular crystal form such as cubic, octahedral, dodecahedral, tetradecahedral, etc., an irregular crystal form such as spherical, tabular, etc., or a composite form of these crystal forms.

The silver halide grains may have a uniform phase throughout the grains or a different phase between the inside and the surface layer thereof.

During the formation or physical ripening of the silver halide grains for use in this invention, a cadmium salt, a sulfite, a lead salt, a thallium salt, a rhodium salt or a complex salt thereof, an iridium salt or a complex salt thereof, etc., may be present.

The silver halide for use in this invention is preferably silver haloiodide prepared in the presence of an iridium salt or a complex salt thereof in an amount of from $10^{-8}$ to $10^{-5}$ mole per mole of silver, wherein the silver iodide content in the surface portion of the grains is greater than the mean silver iodide content of the grains. By using a silver halide emulsion containing such a silver haloiodide, photographic characteristics having higher sensitivity and higher gamma are obtained.

The silver halide emulsion for use in this invention may or may not be chemically sensitized. Chemical sensitizing methods for the silver halide emulsion include sulfur sensitization, a reduction sensitization and a noble metal sensitization. They may be used singly or in combination thereof.

The typical noble metal sensitization is a gold sensitization wherein a gold compound such as gold complex salt is mainly used. Complex salts of other noble metals than gold, such as platinum, palladium, rhodium, etc., may be also used. Examples thereof are described in U.S. Pat. No. 2,448,060 and British Patent 618,061.

For the sulfur sensitization, a sulfur compound contained in gelatin as well as various sulfur compounds such as thiosulfates, thioureas, thiazoles, rhodanines, etc., can be used.

For the chemical sensitization, it is preferred to use an iridium salt or a rhodium salt before the physical ripening, in particular, at the formation of silver halide grains in the production step of the silver halide emulsion.

It is preferred in the point of increasing the maximum density (Dmax) that the silver halide emulsion layer of this invention contains two kinds of monodisperse silver halide emulsions, each containing silver halide grains having a different grain size as disclosed in Japanese Patent Application (OPI) Nos. 223734/86 and 90646/87. Also, the sulfur sensitization is most preferred as chemical sensitization in this invention.

A monodisperse silver halide emulsion containing layered silver halide grains may or may not be chemically sensitized. A monodisperse emulsion containing silver halide grains of large grain size is liable to form black pepper and hence the emulsion is generally chemically sensitized. If a chemical sensitization is applied, it is preferred to shallowly apply the chemical sensitization only to the extent of causing black pepper. The term "shallowly apply" means that the chemical sensitization is performed in a shorter period of time, at a lower temperature, or using a smaller amount of sensitizer than in the case of applying chemical sensitization to a monodisperse emulsion of small grain size.

There is no particular restriction on the sensitivity difference between the monodisperse emulsion of large grain size and the monodisperse emulsion of small grain size but the difference ($\Delta \log E$) is preferably from 0.1 to 1.0, and more preferably from 0.2 to 0.7. In this case, it is preferred that the sensitivity of the monodisperse emulsion of large size is higher.

The sensitivity of the silver halide emulsion is obtained in the case of coating the emulsion containing the hydrazine derivative on a support and developing it using a developer containing at least 0.15 mole/liter of sulfite ion and having pH of from 10.5 to 12.3.

The mean grain size of a monodisperse silver halide emulsion of small grain size is less than 90%, and preferably less than 80% of the mean grain size of the monodisperse silver halide emulsion of large grain size.

The mean grain size of the silver halide grains of the silver halide emulsions is preferably in the range of from 0.02 $\mu$m to 1.0 $\mu$m, and more preferably from 0.1 $\mu$m to 0.5 $\mu$m and it is preferred that both the mean grain sizes of the monodisperse emulsion of large size and the monodisperse emulsion of small size are contained in the aforesaid range.

When two or more kinds of silver halide emulsions each containing silver halide grains having different grain size are used in this invention, the silver coating amount of the monodisperse silver halide emulsion of small size is preferably from 40 to 90% by weight, and more preferably from 50 to 80% by weight to the total silver coated amount of the emulsions.

In this invention, monodisperse emulsions having different grain sizes may be introduced into the same emulsion layer or different emulsion layers. In the latter case, it is preferred that the monodisperse emulsion of large grain size is used for the upper layer and the monodisperse emulsion of small grain size is used for the lower emulsion layer.

In addition, the total silver coating amount is preferably from 1 g/m$^2$ to 8 g/m$^2$ in this invention.

The silver halide photographic emulsions of this invention can contain a sensitizing dye (e.g., a cyanine dye or a merocyanine dye) for increasing the sensitivity as described in Japanese Patent Application (OPI) No. 52050/80, pages 45-55. These sensitizing dyes may be used singly or as a combination thereof. A combination of sensitizing dyes is frequently used for the purpose of super color sensitization.

The silver halide emulsion may contain, together with sensitizing dye(s), a dye showing no spectral sensitizing action by itself or a material which does not substantially absorb visible light and shows super color sensitizing action.

Useful sensitizing dyes, combinations of dyes showing super color sensitization, and materials showing super color sensitization are described in *Research Disclosure*, Vol. 176, No. 17643, page 23, IV-J (December, 1978).

The photographic light-sensitive materials of this invention can also contain various compounds for preventing the formation of fog during the production, storage, and processing of the light-sensitive materials or for stabilizing the photographic performance. For example, there are antifoggants and stabilizers such as azoles (e.g., benzothiazolium salts, nitroindazoles, chlorobenzimidazoles, bromobenzimidazoles, mercaptobenzimidazoles, mercaptobenzothiazoles, mercaptothiadiazoles, aminotriazoles, benzothiazoles, nitrobenzotriazoles, etc.), mercaptopyrimidines, mercaptotriazines, thioketone compounds (e.g., oxazolinethione), azaindenes (e.g., triazaindenes, tetraazaindenes (in particular, 4-hydroxy-substituted (1,3,3a,7)tetraazaindenes) pentaazaindenes, etc.), benzenethiosulfonic acid, benzenesulfinic acid, and benzenesulfonic acid amide.

Of the aforesaid compounds, benzotriazoles (e.g., 5-methylbenzotriazole) and nitroindazoles (e.g., 5-nitroindazole) are preferred. These compounds may be incorporated in processing solutions.

In this invention, development accelerators and accelerators for nucleating infectious development can be used. Suitable compounds are described in Japanese Patent Application (OPI) Nos. 77616/78, 37732/79, 137133/78, 140340/85, and 14959/85. Also, various compounds containing nitrogen atoms or sulfur atoms can be also used as such accelerators.

The amount of the accelerator used depends upon the kind of the compound but is preferably from $1.0 \times 10^{-3}$ to 0.5 g/m$^2$, and more preferably from $5.0 \times 10^{-3}$ to 0.1 g/m$^2$ of the photographic material.

The photographic light-sensitive materials of this invention may contain a desensitizer in the silver halide emulsion layer or other hydrophilic colloid layer thereof.

In an organic desensitizer for use in this invention, the sum of the polarographic half wave potentials thereof, that is, the sum of the polarographic anodic potential and cathodic potential defined by the oxidation-reduction potential determined by polarography, becomes positive. The measurement method of the oxidation-reduction potential of polarography is described, for example, in U.S. Pat. No. 3,501,307. It is preferred that the organic desensitizer contains at least one water-solubilizing group and examples of such group are a sulfonic acid group, a carboxylic acid group, and a phosphonic acid group. These groups may form salts with organic bases such as ammonia, pyridine, triethylamine, piperidine, morpholine, etc. or an alkali metal (e.g., sodium and potassium).

Preferred organic desensitizers for use in this invention are those represented by formulas (III) to (V) described in Japanese Patent Application No. 280998/76.

It is preferred in this invention that the organic desensitizer is present in the silver halide emulsion layer in an amount of from $1.0 \times 10^{-8}$ to $1.0 \times 10^{-4}$ mole/m$^2$, particularly from $1.0 \times 10^{-7}$ to $1.0 \times 10^{-5}$ mole/m$^2$ of the photographic material.

The photographic light-sensitive materials may contain water-soluble dyes in the silver halide emulsion layers or other hydrophilic colloid layers which function as filter dyes, irradiation preventing dyes, or for other various purposes.

As filter dyes, there are dyes further lowering the photographic sensitivity, preferably ultraviolet absorbents having the spectral absorption maximum in the specific sensitivity region of silver halide, and dyes having substantial light absorption mainly in the wavelength region from 380 n.m. to 600 n.m. for increasing the safety to a safe light in the case of handling the light-sensitive material for bright room work.

It is preferred such a dye is incorporated in the silver halide emulsion layer or in an insensitive hydrophilic colloid layer disposed over or above the emulsion layer together with a mordant.

The amount of the ultraviolet absorbent added depends upon the molar extinction coefficient thereof but is usually from $10^{-2}$ g/m$^2$ to 1 g/m$^2$, and preferably from 50 mg/m$^2$ to 500 mg/m$^2$ of the photographic material.

The aforesaid ultraviolet absorbents can be added to a coating composition for the photographic layer as a solution in a proper solvent such as water, in alcohol (e.g., methanol, ethanol, and propanol), acetone, methylcellosolve, etc., or a mixture thereof.

As the ultraviolet absorbents, there are, for example, aryl-substituted benzotriazole compounds, 4-thiazolidone compounds, benzophenone compounds, cinnamic acid ester compounds, butadiene compounds, benzoxazole compounds and ultraviolet absorptive polymers.

Examples of ultraviolet absorbents are described in U.S. Pat. Nos. 3,533,794, 3,314,794, and 3,352,681, Japanese Patent Application (OPI) No. 2784/71, U.S. Pat. Nos. 3,705,805, 3,707,375, 4,045,229, 3,700,455, and 3,499,762, West German Patent (OLS) 1,547,863.

As the filter dyes, there are oxonol dyes, hemioxonol dyes, styryl dyes, merocyanine dyes, cyanine dyes, and azo dyes. From the point of reducing color residue after processing water-soluble dyes and dyes, decoloring by alkali or sulfite ions are preferred.

Practical examples of the filter dyes are pyrozoloneoxonol dyes described in U.S. Pat. No. 2,274,782; diarylazo dyes described in U.S. Pat. No. 2,956,879; styryl dyes and butadienyl dyes described in U.S. Pat. Nos. 3,423,207 and 3,384,487; merocyanine dyes described in U.S. Pat. No. 2,527,583; merocyanine dyes and oxonol dyes described in U.S. Pat. Nos. 3,486,897, 3,652,284, and 3,718,472; enaminohemioxonol dyes described in U.S. Pat. No. 3,976,661, and dyes described in British Pat. Nos. 584,609 and 1,177,429, Japanese Patent Application (OPI) Nos. 85130/73, 99620/74, and 114420/74, U.S. Pat. Nos. 2,533,472, 3,148,187, 3,177,078, 3,247,127, 3,540,887, 3,575,704, and 3,653,905.

The dyes are added to coating compositions for insensitive hydrophilic colloid layers as a solution in a proper solvent such as water, an alcohol (e.g., methanol, ethanol, and propanol), acetone, methylcellusolve, etc.

The amount of the dye is generally from $10^{-3}$ g/m$^2$ to 1 g/m$^2$, and preferably from $10^{-3}$ g/m$^2$ to 0.5 g/m$^2$ of the photographic material.

The photographic light-sensitive material of this invention may contain an inorganic or organic hardening agent in the photographic emulsion layer(s) or other hydrophilic colloid layer(s). Examples thereof are chromium salts, aldehydes (formaldehyde, glutal aldehyde, etc.,), active vinyl compounds (1,3,5-triacryloyl-hexahydro-s-triazine, 1,3-vinylsulfonyl-2-propanol, etc.), active halogen compounds (2,4-dichloro-6-hydroxy-s-triazine, etc.), and mucohalogenic acids. They can be used singly or as a combination thereof.

The photographic light-sensitive materials of this invention may further contain in the photographic emulsion layers or other hydrophilic colloid layers various surface active agents for the purposes of coating aid, static prevention, slidability improvement, dispersibity improvement, sticking prevention, and improvement of photographic properties (e.g., development acceleration, increase of contrast, and sensitization).

The surface active agents which are preferably used in this invention are polyalkylene oxides having a molecular weight of at least 600 which are described in Japanese Patent Publication No. 9412/83.

In the case of using as antistatic agent, surface active agents having fluorine as described in U.S. Pat. No. 4,201,586 and Japanese Patent Application (OPI) Nos. 80849/85 and 74554/84 are particularly preferred.

The photographic light-sensitive materials of this invention may further contain in the photographic emulsion layers or other hydrophilic colloid layers, a matting agent such as silica, magnesium oxide, polymethylmethacrylate particles, etc., for sticking prevention.

The photographic emulsion layers in this invention can further contain a dispersion of a water-insoluble or a sporingly water-soluble synthetic polymer for improving the dimensional stability. Examples the polymer are polymers or copolymers composed of an alkyl (meth)acrylate, an alkoxyacryl (meth)acrylate, glycidyl (meth)acrylate, etc. The polymers may be used singly or as a composition thereof which may include another monomer such as acrylic acid, methacrylic acid, etc.

Also, the photographic light-sensitive materials of this invention preferably contain a compound having an acid group in the photographic emulsion layers and other hydrophilic colloid layers. As the compound having an acid group, there are organic acids such as salicyclic acid, acetic acid, ascorbic acid, etc., and polymers or copolymers having an acid monomer such as acrylic acid, maleic acid, phthalic acid, etc., as a recuring unit. These compounds are described in Japanese Patent Application (OPI) Nos. 223834/76, 228437/86, 25745/87, and 55642/87. In these compounds, ascorbic acid is particularly preferred as a low molecular weight compound and a water-dispersible latex of copolymer comprising a crosslinking monomer having an acid monomer such as acrylic acid and two or more unsaturated groups such as divinylbenzene is also particularly preferred as a high molecular weight compound.

For obtaining very high contrast and highly sensitive photographic characteristics using the silver halide photographic material of this invention, a stable developer can be used without the need of using a conventional infectious developer and a high alkali developer having a pH of about 13 described in U.S. Pat. No. 2,419,975.

That is, in the case of using the silver halide photographic material of this invention, sufficiently high contrast negative images can be obtained by using a developer containing at least 0.15 mole/liter of sulfite ion as a preservative and having pH of from 10.5 to 12.3, and particularly from 11.0 to 12.0.

There is no particular restriction on the developing agent which is used for photographic materials of this invention but dihydroxybenzenes are preferred because they give good dot images. A combination of a dihydroxybenzene and a 1-phenyl-3-pyrazolidone or a combination of a dihydroxybenzene and a p-aminophenol is, as the case may be, used.

The developing agent is preferably used in the amount of from 0.05 mole/liter to 0.8 mole/liter. Also, when a combination of a dihydroxybenzene and a 1-phenyl-3-pyrazolidone or a p-aminophenol is used, it is preferred that the former is used in the amount of from 0.05 mole/liter to 0.5 mole/liter and the latter less then 0.06 mole/liter.

As the sulfite which is used as a preservative in this invention, there are sodium sulfite, potassium sulfite, lithium sulfite, ammonium sulfite, sodium hydrogensulfite, potassium metahydrogensulfite, sodium formaldehydehydrogensulfite, etc. The sulfite is used in an amount of preferably at least 0.4 mole/liter, and particularly at least 0.5 mole/liter.

The developer in this invention can contain a compound described in Japanese Patent Application (OPI) No. 24347/81 as a silver stain preventing agent.

The developer may contain a compound described in Japanese Patent Application (OPI) No. 267759/86 as a dissolution aid. Furthermore, the developer may contain a compound described in Japanese Patent Application (OPI) No. 93433/85 or a compound described in Japanese Patent Application No. 28708/76 as a pH buffer.

The compound represented by formula (I) described above for use in this invention can be also used in combination with an internal latent image type silver halide emulsion in addition to the aforesaid combination with a negative working silver halide emulsion as a high contrast photographic light sensitive material.

In this case, the compound of formula (I) is preferably incorporated in an internal latent image type silver halide emulsion layer but may be incorporated in a hydrophilic colloid layer adjacent to the internal latent image type silver halide emulsion layer. Examples of such a hydrophilic colloid layer include a coloring material layer, an interlayer, a filter layer, a protective layer, an antihalation layer, etc. One of the aforesaid layers can be employed if the layer does not disturb the diffusion of a nucleating agent into the silver halide grains.

It is preferred that the content of the compound represented by formula (I) in the aforesaid layer is the amount capable of giving the sufficient maximum density (e.g., above 1.0 as silver density) in the case of developing the internal latent image type silver halide emulsion by a surface developer. However, since the content thereof depends upon the characteristics of the silver halide emulsion being used, the chemical structure of the nucleating agent, and the developing condition, the amount can be varied in a wide range but the useful amount thereof is in the range of from about 0.005 mg to 500 mg, preferably from about 0.01 mg to 100 mg per mole of silver in the internal latent image silver halide emulsion.

In the case of incorporating the compound in a hydrophilic colloid layer adjacent to the internal latent image type silver halide emulsion layer, the compound may be incorporated in the hydrophilic colloid layer in the aforesaid amount to the amount of silver contained the same area of the emulsion layer. The definition of the internal latent image type silver halide emulsion is described in Japanese Patent Application (OPI) No. 170733/86, page 10, upper column and British Patent 2,089,057, pages 18 to 20.

Furthermore, preferred internal latent image type emulsions which can be used in this invention are described in Japanese Patent Application No. 253716/86 and preferred silver halide grains are described in the same patent application.

The internal latent image type silver halide emulsions for the photographic light-sensitive materials of this invention may be spectrally sensitized to blue light having relatively long wavelength, green light, red light, or infrared light using sensitizing dye(s). Examples of the sensitizing dyes are cyanine dyes, merocyanine dyes, complex cyaninde dyes, complex cyanine dyes, holopolar cyanine dyes, styryl dyes, hemicyanine dyes, oxonol dyes, and hemioxanol dyes. These sensitizing dyes are described in Japanese Patent Application (OPI) Nos. 40638/84, 40636/84 and 38739/84.

The photographic light-sensitive materials of this invention can contain color image-forming couplers as coloring materials or can be developed by developers containing color image-forming couplers.

Specific examples of the cyan, magenta, and yellow couplers for use in this invention are described in the patents cited in *Research Disclosure*, No. 17643, VII-D, (December, 1978) and R.D., No. 18717 (November, 1979).

For the photographic materials of this invention, couplers giving colored dyes having a proper diffusibility, DIR couplers releasing a development inhibitor with a coupling reaction, or couplers releasing a development accelerator with a coupling reaction can be used.

As yellow coupler which can be used in this invention, there are oil protective type acylacetamide series couplers as typical examples.

In this invention, two equivalent yellow couplers are preferably used and typical examples thereof are oxygen atom-releasing type yellow couplers and nitrogen atom-releasing type yellow couplers. In these couplers, α-pivaloylacetanilide series yellow couplers are excellent in fastness, and in particular, the light fastness of the colored dyes formed, while α-benzoylacetanilide series yellow couplers give high coloring density.

As the magenta couplers for use in this invention, there are oil-protective type indazolone series or cyanoacetyl series magenta couplers, preferably 5-pyrazolone series magenta couplers and pyrazoloazole series magenta couplers such as pyrazolotriazole series couplers. The pyrazolone series couplers having an arylamino group or an acylamino group at the 3-position thereof are preferred from the viewpoint of the hue of the colored dyes and the coloring density.

Preferred releasing groups for the two equivalent 5-pyrazolone series magenta couplers include nitrogen atom-releasing groups described in U.S. Pat. No. 4,310,619 and arylthio groups described in U.S. Pat. No. 4,351,897. Also, 5-pyrazolone series magenta couplers having a ballast group described in European Patent 73,636 give high coloring density.

Pyrazole series magenta couplers include pyrazolobenzimidazoles described in U.S. Pat. No. 3,369,899, preferably pyrazole{5,1-c}{1,2,4}triazoles described in U.S. Pat. No. 3,725,067, pyrazolotetrazoles described in *Research Disclosure*, No. 24220 (June, 1984) and pyrazolopyrazoles described in R.D., No. 24230 (June 1984). From the view point of less yellow side absorption of colored dyes and high light fastness of colored dyes, imidazo{1,2-b}pyrazoles described in European Patent 119,741 are preferred and pyrazolo{1,5-b}{1,2,4}triazoles described in European Patent 119,860 are particularly preferred.

Cyan couplers for use in this invention include oil-protective type naphtholic and phenolic couplers.

The naphtholic cyan couplers include naphtholic couplers described in U.S. Pat. No. 2,474,293 and preferably, oxygen atom-releasing type two equivalent naphtholic couplers described in U.S. Pat. Nos. 4,052,212, 4,146,396, 4,228,233 and 4,296,200.

Also, specific examples of the phenolic cyan couplers are described in U.S. Pat. Nos. 2,369,929, 2,801,171, 2,772,162, and 2,895,826 Cyan couplers having high fastness to moisture and heat are preferably used in this invention. Typical examples thereof are the phenolic cyan couplers having an alkyl group of two or more carbon atoms at the metaposition of the phenol nucleus as described in U.S. Pat. No. 3,772,002, 2,5-diacylamino-substituted phenolic cyan couplers and phenolic couplers having a ureido group at the 2-position and an acylamino group at the 5-position thereof.

It is preferred that the color photographic material of this invention contains colored couplers together with magenta and cyan couplers for correcting unnecessary adsorptions at the short wavelength region by the dyes formed from the magenta coupler and the cyan coupler.

In this invention, the graininess of the color images formed can be improved by using couplers producing colored dyes having a proper diffusibility together with the aforesaid couplers. About such couplers producing diffusible dyes, specific examples of the magenta couplers are described in U.S. Pat. No. 4,366,237 and British Patent 2,125,570. Specific examples of the yellow, magenta and cyan couplers are described in European Patent 96,570 and West German Patent Application (OLS) No. 3,234,533.

The dye-forming couplers and specific couplers described above may form a dimer or higher polymer. Typical examples of the polymerized dye-forming couplers are described in U.S. Pat. Nos. 3,451,820 and 4,080,211. Also, specific examples of the polymerized magenta couplers are described described in British Patent 2,102,173 and U.S. Pat. No. 4,367,282.

The couplers can be used in one light-sensitive emulsion layer as a mixture of two or more for meeting the properties required for the color photographic material or the same kind of coupler may be incorporated in two or more photographic layers.

A standard amount of the color coupler is in the range of from 0.001 mole to 1 mole per mole of the light-sensitive silver halide in the silver halide emulsion layer, with from 0.01 mole to 0.5 mole of a yellow coupler, from 0.003 mole to 0.3 mole of a magenta coupler, and from 0.002 mole to 0.3 mole of a cyan coupler, per mole of the light-sensitive silver halide being preferred.

The silver halide photographic emulsions in this invention can be also used for obtaining desired transferred images in an image-receiving layer. This can be performed by proper processing in a combination of dye image-providing compounds (coloring materials) for color diffusion transfer capable of releasing a diffusible dye corresponding to the development of the silver halide. Various coloring materials are known for color duffusion transfer process. In particular, a coloring material which is originally non-diffusible but is cleaved by the oxidation-reduction reaction with the oxidation product of a developing agent or an electron transferring agent (hereinafter, the coloring materials are referred to as DRR compound) is preferred. In these compounds, a DRR compound having a N-substituted sulfamoyl group is preferred. In particular, the DRR compounds having an o-hydroxyarylsulfonamyl group as described in U.S. Pat. Nos. 4,055,428, 4,053,312, and 4,336,322 and the DRR compounds having a redox mother nucleus as described in Japanese Patent Application (OPI) 149328/78 are preferred in the case of using thereof together with the nucleating agents for use in this invention. In the case of using the nucleating agents together with such DRR compounds, the temperature dependence at processing is remarkably less.

Specific examples of DRR compounds are, in addition to those described in the aforesaid patents, magenta dye image-forming materials such as 1-hydroxy-2-tetramethylsulfamoyl-4-{3'-methyl-4'-(2''-hydroxy-4'''-methyl-5''-hexadecyloxyphenylsulfamoyl)-phenylazo}-naphthalene, etc., and yellow dye image-forming materials such as 1-phenyl-3-cyano-4 ( 2''',4'''-di-tert-pentylphenoxyacetamino)-phenylsulfamoyl}-phenylazo-5-pyrazolone, etc.

The details of color couplers which are preferably used in this invention are described in aforesaid Japanese Patent Application (OPI) No. 149328/78.

For forming direct positive color images using the photographic light-sensitive material of this invention, it is preferred to form the color images by imagewise exposing the photographic material, then, after or while applying thereto a fogging treatment by light or a nucleating agent, developing with a surface developer containing an aromatic primary amino color developing agent, bleaching and fixing (or blixing). The pH of the developer is preferably in the range of 10.0 to 11.0.

For the fogging treatment in this invention, a so-called "light fogging method", i.e., a method of applying second light exposure onto the surface of the light-sensitive layer or a so-called "chemical fogging method", i.e., a method of developing in the presence of a nucleating agent may be used.

Furthermore, the photographic light-sensitive material of this invention may be developed in the presence of a nucleating agent and light for fogging or the photographic light-sensitive material containing a nucleating agent may be subjected to fogging light ex-osure.

The light fogging method is described in Japanese Patent Application No. 253716/76.

Also, nucleating agents which can be used in this invention are described in the aforesaid patent application and the compounds represented by {N-I} and {N-II} in the aforesaid patent application are particularly preferred. Examples of these preferred compounds are compounds {N-I - 1} to {N-II -}10 and compounds {N-II - 1} to {N-II - 12} illustrated in the patent application.

In this invention, a nucleating accerator may be used for the fogging treatment and they are described in aforesaid Patent Application No. 253716/76. Examples of the nucleation accelerator are compounds (A - 1) to (A - 13) illustrated in the same patent application.

A color developing agent which is used for developing the photographic light-sensitive materials of this invention is described, for example, in the aforesaid patent application and as an aromatic primary amino color developing agent, a p-phenylenediamine series compound is preferred. Typical examples thereof are 3-methyl-4-amino-N-ethyl-N-($\beta$-methanesulfonamidoethyl)aniline, 3-methyl-4-amino-N-ethyl-N-($\beta$-hydroxyethyl)aniline, 3-methyl-4-amino-N-ethyl-N-methoxyethylaniline, and the salts thereof, such as sulfates and hydrochlorides.

For forming direct positive color images by a color diffusion transfer process using the photographic light-sensitive material of this invention, a black and white developing agent such as a phenidone derivative, etc., can be used in addition to the aforesaid color developing agent.

After color development, the photographic emulsion layer(s) are usually bleached. The bleach may be carried out simultaneously with (i.e., single-bath blix) or separately from a fixation step. Furthermore, for quickening the processing, a processing system of performing the blix after bleaching may be employed or a system of performing the blix after fixing step may be employed.

For the bleach solution or blix solution for use in this invention may further contain various additives as described, for example, in Japanese Patent Application No. 215272/82.

After the desilvering step (i.e., blix or fix), wash and/or stabilization is applied. For the wash or stabilization process, it is preferred to use water which has been subjected to a softening treatment. As the softening treatment method, there are a method of using ion exchange resins as described in Japanese Patent Application (OPI) No. 288838/87 and a method of using a back osmosis means as described in the same patent application. Examples of these methods are also described in the patent application.

Furthermore, compounds described in Japanese Patent Application (OPI) No. 215272/87 can be also used for the wash step and the stabilization step as additives.

It is preferred that the amount of a replenisher for each processing step is less. The amount of the reprenisher is preferably from 0.1 to 50 times, and more preferably from 3 to 30 times the amount carried by a unit area of the photographic material from the pre-bath.

Then, the following examples serve to illustrate the invention without limiting, however, the scope of the invention. Unless indicated otherwise, all parts, percents, ratios and the like are by weight.

EXAMPLE 1

A multilayer color photographic material (No. A) having the following layers on a paper support, both surfaces of which were coated with polyethylene was prepared. The polyethylene coating on the support at the emulsion layer carrying side contained titanium diozide as a white pigment and ultramarine blue as a bluish dye.

In the following layer construction, the numeral in the composition of each layer is a coated amount shown by $g/m^2$, in which, however, the numerals for silver halide emulsion and colloid silver are shown by the calculated amount of silver and the numeral for spectral sensitizing dye, nucleating agent, and nucleation accelerator is shown by mole per mole of silver halide in the same silver halide emulsion layer.

| Layer E1: | |
|---|---|
| Silver Halide Emulsion A | 0.26 |
| Spectral Sensitizing Dye (ExSS-1) | $1.0 \times 10^{-4}$ |
| Spectral Sensitizing Dye (ExSS-2) | $6.1 \times 10^{-5}$ |
| Gelatin | 1.11 |
| Cyan Coupler (ExCC-1) | 0.21 |
| Cyan Coupler (ExCC-2) | 0.26 |
| Ultraviolet Absorbent (ExUV-1) | 0.17 |
| Solvent (ExS-1) | 0.23 |
| Development Controlling Agent (ExGC-1) | 0.02 |
| Stabilizer (ExA-1) | 0.006 |
| Nucleation Accelerator (ExZS-1) | $3.0 \times 10^{-4}$ |
| Nucleating Agent (ExZK-1) | $8.0 \times 10^{-5}$ |
| Layer E2: | |
| Gelatin | 1.41 |
| Color Mixing Preventing Agent (ExKB-1) | 0.09 |
| Solvent (ExS-1) | 0.10 |
| Solvent (ExS-2) | 0.10 |
| Layer E3: | |
| Silver Halide Emulsion A | 0.23 |
| Spectral Sensitizing Dye (ExSS-3) | $3.0\ 10^{-4}$ |
| Gelatin | 1.05 |
| Magenta Coupler (ExMC-1) | 0.16 |
| Color Image Stabilizer (ExSA-1) | 0.20 |
| Solvent (ExS-3) | 0.25 |
| Development Controlling Agent (ExGC-1) | 0.02 |
| Stabilizer (ExA-1) | 0.006 |
| Nucleation Accelerator (ExZS-1) | $2.7 \times 10^{-4}$ |
| Nucleating Agent (ExZK-1) | $1.4 \times 10^{-4}$ |
| Layer E4: | |
| Gelatin | 0.47 |
| Color Mixing Preventing Agent (ExKB-1) | 0.03 |
| Solvent (ExS-1) | 0.03 |
| Solvent (ExS-2) | 0.03 |
| Layer E5: | |

-continued

| | |
|---|---|
| Colloid Silver | 0.09 |
| Gelatin | 0.49 |
| Color Mixing Preventing Agent (ExKB-1) | 0.03 |
| Solvent (ExS-1) | 0.03 |
| Solvent (ExS-2) | 0.03 |
| Layer E6: | |
| Same as Layer E4 | |
| Layer E7: | |
| Silver Halide Emulsion A | 0.40 |
| Spectral Sensitizing Dye (ExSS-3) | $4.2 \times 10^{-4}$ |
| Gelatin | 2.17 |
| Yellow Coupler (ExYC-1) | 0.51 |
| Solvent (ExS-2) | 0.20 |
| Solvent (ExS-4) | 0.20 |
| Development Controlling Agent (ExGC-1) | 0.06 |
| Stabilizer (ExA-1) | 0.001 |
| Nucleation Accelerator (ExZS-1) | $5.0 \times 10^{-4}$ |
| Nucleating Agent (ExZK-1) | $1.2 \times 10^{-5}$ |
| Layer E8: | |
| Gelatin | 0.54 |
| Ultraviolet Absorbent (ExUV-2) | 0.21 |
| Solvent (ExS-4) | 0.08 |
| Layer E9: | |
| Gelatin | 1.28 |
| Acryl-Modified Copolymer of Polyvinyl Alcohol (modified degree of 17%) | 0.17 |
| Fluid Paraffin | 0.03 |
| Latex Particles (mean particle size of 2.8 μm) of Methyl Polymethacrylate | 0.05 |
| Layer B1: | |
| Gelatin | 8.70 |
| Layer B2: | |
| Same of Layer E9. | |

In addition, Layer B1 and Layer B2 are back layers.

Each layer further contained a gelatin hardening agent (ExGK-1) and a surface active agent in addition to the aforesaid components.

Silver Halide Emulsion A:

An aqueous solution of potassium bromide and sodium chloride and an aqueous solution of silver nitrate were simultaneously added to an aqueous gelatin solution containing 0.5 g of 3,4-dimethyl-1, 3-thiazoline-2-thione and 0.3 g of lead acetate per mole of silver with vigorous stirring over a period of about 5 minutes to provide a monodisperse silver chlorobromide emulsion having a mean grain size of about 0.2 μm and a silver bromide content of 40 mole %. Chemical sensitization was performed by adding to the emulsion 35 mg of sodium thiosulfate and 20 mg of chloroauric acid (tetrahydrate) per mole of silver followed by heating the emulsion for 60 minutes.

Then, the same silver halide growing operation as above was applied to the silver halide emulsion using the silver chlorobromide grains as core under the same condition as above to provide a monodisperse core/-shell silver chlorobromide emulsion having a mean grain size of 0.4 μm. The variation coefficient of the grain sizes thereof was about 10%.

To the emulsion were added 3 mg of sodium thiosulfate and 3.5 mg of chloroauric acid (tetrahydrate) per mole of silver followed by heating for 50 minutes to perform the chemical sensitization of the emulsion, whereby the internal latent image-type silver halide emulsion (Emulsion A) was obtained.

The compounds used for preparing the sample were as follows.

(ExCC-1) Cyan Coupler:

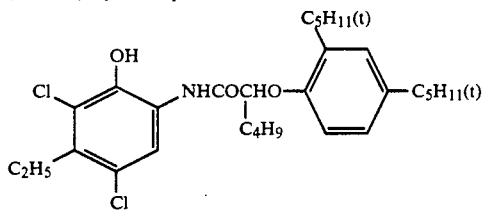

(ExCC-2) Cyan Coupler:

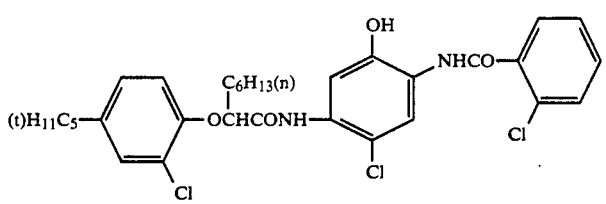

(ExMC-1) Magenta Coupler:

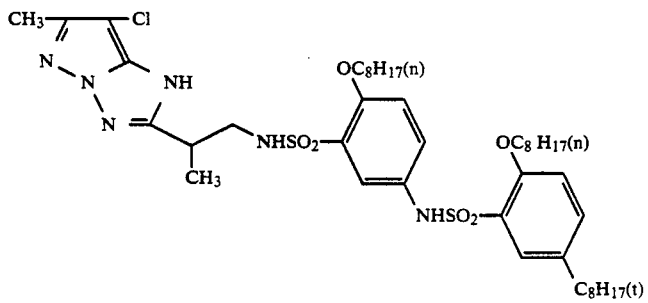

(ExYC-1) Yellow Coupler:

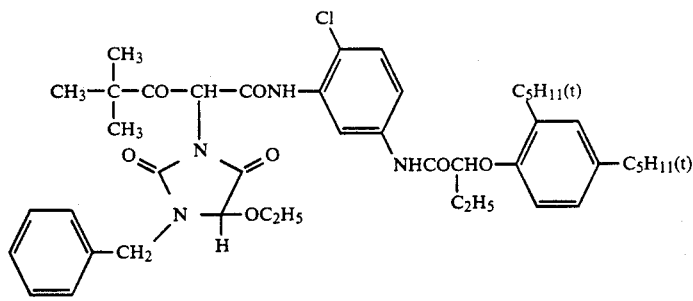
(ExSS-1) Spectral Sensitizing Dye:
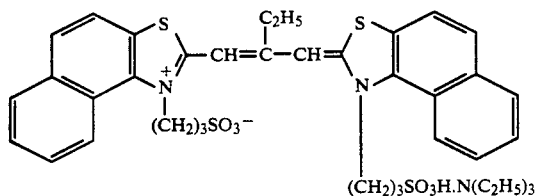
(ExSS-2) Spectral Sensitizing Dye:
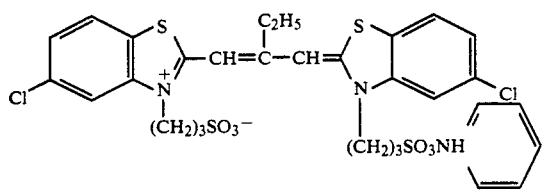
(ExSS-3) Spectral Sensitizing Dye:
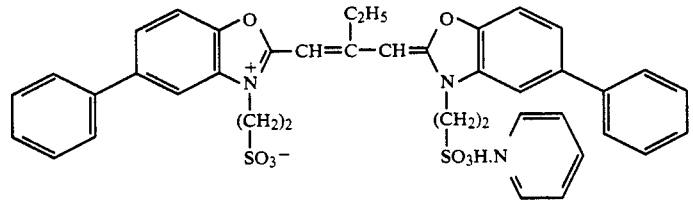
(ExSS-4) Spectral Sensitizing Dye:
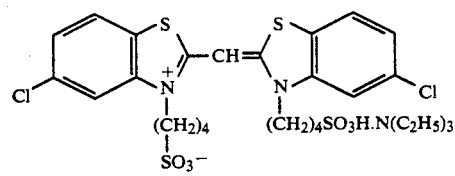
(ExS-1) Solvent:
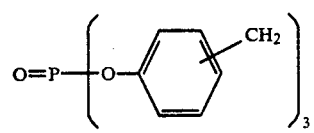
(ExS-2) Solvent:
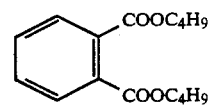
(ExS-3) Solvent:

-continued

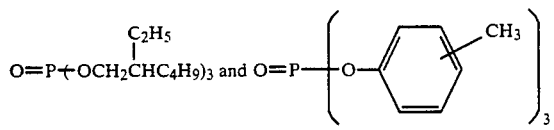

1:1 mixture (volume ratio)

(ExS-4) Solvent:
O=P(̵O—C₇H₁₉(iso))₃

(ExUV-1) Ultraviolet Absorbent:

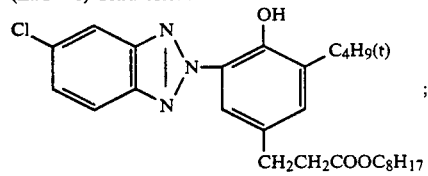 (1)

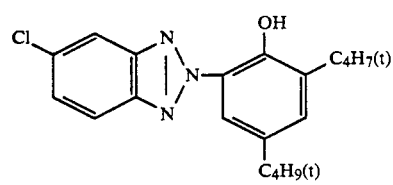 (2)

and

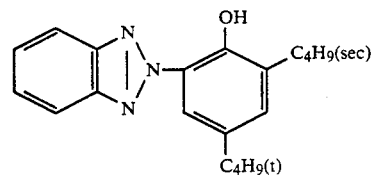 (3)

5:8:9 mixture (weight ratio)

(ExUV-2) Ultraviolet Absorbent
2:9:8 Mixture (weight ratio) of above
(1), (2) or (3)

(ExSA-1) Color Image Stabilizer:

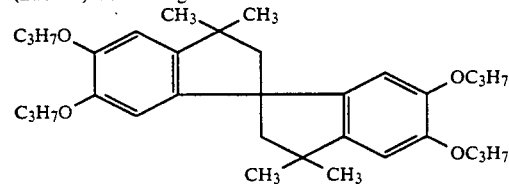

(ExKB-1) Color Mixing Presenting Agent:

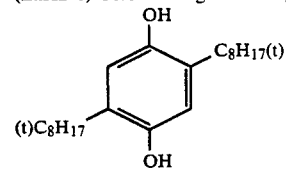

(ExGC-1) Development Controlling Agent:

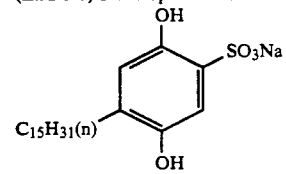

(ExA-1) Stabilizer:
4-hydroxy-5,6-trimethylene-1,3,3a,7-tetra-azaindene
(ExZS-1) Nucleation Accelerator:
2-(3-dimethylaminopropylthio)-5-mercapto-1,3,4-thiadiazole chlorhydride (ExZK-1) Nucleating Agent:

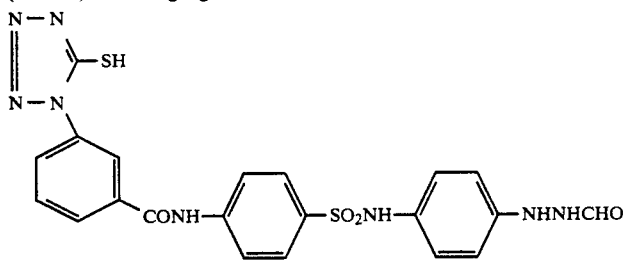

(ExGK-1) Gelatin Hardening:
1-Oxy-3,5-dichloro-s-triazine Sodium Salt

The sample was wedge-exposed (1/10 sec., 10 CMS) and then processed according to Processing step A shown below.

| Processing Step A: | | |
|---|---|---|
| | Time | Temperature |
| Color Development | 100 sec. | 38° C. |
| Blix | 30 sec. | 38° C. |
| Wash (1) | 30 sec. | 38° C. |
| Wash (2) | 30 sec. | 38° C. |

The replenishing system for wash water was performed by a so-called countercurrent replenishing system which comprises replenishing the replenisher to wash bath (2) and introducing overflown liquid from wash bath (2) into wash bath (1).

| | Mother liquid |
|---|---|
| Color Developer | |
| Diethylenetriaminetetraacetic Acid | 0.5 g |
| 1-Hydroxyethylydene-1,1-diphosphonic Acid | 0.5 g |
| Diethylene Glycol | 8.0 g |
| Benzyl Alcohol | 10.0 g |
| Sodium Bromide | 0.5 g |
| Sodium Chloride | 0.7 g |
| Sodium Sulfite | 2.0 g |
| N,N-diethylhydroxylamine | 3.5 g |
| 3-Methyl-4-amino-N-ethyl-N-($\beta$-methanesulfonamidoethyl)aniline | 6.0 g |
| Potassium Carbonate | 30.0 g |
| Fluorescent Whitening Agent (stilbene series) | 1.0 g |
| Pure Water to make | 1 liter |
| pH | 10.50 |
| The pH was adjusted with potassium hydroxide or hydrochloric acid. | |
| Blix Solution | |
| Ammonium Thiosulfate | 110 g |
| Sodium Hydrogensulfite | 10 g |
| Ethylenediaminetetraacetate Iron(III) Ammonium Dihydrate | 40 g |
| Ethylenediaminetetraacetate Di-sodium.Di-hydrate | 5 g |
| 2-Mercapto-1,3,4-triazole | 0.5 g |
| Pure Water to make | 1 liter |
| pH | 7.0 |
| The pH was adjusted with aqueous ammonia or hydrochloric acid. | |
| Wash Water | |
| Pure water was used. | |

Now, pure water herein used was obtained by treating city water with ion exchange resins to reduce all cation concentration except hydrogen ion and all anion concentration except hydroxide ion below 1 ppm.

Then, by following the same procedure as in preparing Sample No. A described above, except that each of the compounds (nucleating agents) shown in Table 1 below were used in place of the nucleating agent (ExZK-1), multilayer color photographic materials (Sample Nos. 1 to 11) of this invention were prepare.

Each of the samples was wedge-exposed as above and processed by Processing Step A described above.

Then, the density of the cyan colored image of each sample thus processed was measured. The results obtained are shown in Table 1.

TABLE 1

| Sample No. | Nucleating Agent | Cyan Image Dmax | Density Dmin |
|---|---|---|---|
| 1 | Compound (1) | 2.2 | 0.11 |
| 2 | Compound (2) | 2.1 | 0.11 |
| 3 | Compound (4) | 2.2 | 0.11 |
| 4 | Compound (5) | 2.2 | 0.11 |
| 5 | Compound (6) | 2.1 | 0.11 |
| 6 | Compound (7) | 2.1 | 0.11 |
| 7 | Compound (8) | 2.1 | 0.11 |
| 8 | Compound (9) | 2.1 | 0.11 |
| 9 | Compound (10) | 2.1 | 0.11 |
| 10 | Compound (14) | 2.1 | 0.11 |
| 11 | Compound (16) | 2.1 | 0.11 |
| 12 | Compound (17) | 2.1 | 0.11 |
| 13 | Compound (18) | 2.1 | 0.11 |
| A | ExZK-1 | 1.5 | 0.12 |

The amount of each nucleating agent shown above was equivalent to the amount of ExZK-1.

As shown in the above table, Sample Nos. 1 to 13 using the nucleating agents in this invention show high maximum image density (Dmax) as compared with the comparison sample (Sample No. A).

In addition, almost the same results as above were obtained as to the magenta density and the yellow density.

EXAMPLE 2

After simultaneously adding an aqueous silver nitrate solution and an aqueous sodium chloride solution to an aqueous gelatin solution kept at 40° C. in the presence of $5.0 \times 10^{-6}$ mole of $(NH_4)_3RhCl_6$ per mole of silver, soluble salts were removed by a conventional method and after adding thereto gelatin, 2-methyl-4-hydroxy-1,3,3a,7-tetraazaindene was added as a stabilizer without applying chemical ripening. The silver halide emulsion was a monodisperse emulsion containing silver halide grains having a mean grain size of 0.2 $\mu$m and a cubic crystal form.

Then, after adding the hydrazine compound of this invention or a comparison hydrazine compound to the emulsion as shown in Table 2 below, a polyethyl acrylate was added in an amount of 30% by weight based on the amount of gelatin as solid component and after further adding thereto 1,3-vinylsulfonyl-2-propanol as a film hardening agent, the emulsion thus obtained was coated onto a polyester support at a silver coverage of 3.8 g/m². Then, a layer of gelatin (1.8 g/m²) was formed on the emulsion layer as a protective layer.

Each of the samples thus prepared was exposed through an optical wedge using a bright room printer P-607 (made by Dainippon Screen Mfg. Co., Ltd.) (Sample A containing no organic desensitizer was exposed through an assembly of the optical wedge and ND filter having density of 2.0), developed by a developer having the composition shown below for 30 seconds at 38° C., fixed, washed and dried.

| Developer | |
|---|---|
| Hydroquinone | 45.0 g |
| N-Methyl-p-aminophenol Disulfate | 0.8 g |
| Sodium Hydroxide | 18.0 g |
| Potassium Hydroxide | 55.0 g |
| 5-Sulfosalicylic Acid | 45.0 g |
| Boric Acid | 25.0 g |
| Potassium Sulfite | 110.0 g |
| Ethylenediaminetetraacetic Acid Di-sodium Salt | 1.0 g |
| Potassium Bromide | 6.0 g |
| 5-Methylbenzotriazole | 0.6 g |
| n-Butyl diethanolamine | 15.0 g |
| Water to make | 1 liter |
| pH | 11.6 |

Then, the photographic properties obtained were measured and the results are shown in Table 2 below.

TABLE 2

| Sample | Compound Kind | Amount (mg/m²) | Sensitivity *1 (relative value) | Gradation (γ) |
|---|---|---|---|---|
| Comparison Sample a | Comparison Compound A | 37 | 0 | 7.5 |
| Comparison Sample b | Comparison Compound B | 12 | +0.10 | 5.0 |
| Sample 1-1 | Compound (1) | 9 | +0.05 | 20.0 |
| Sample 1-2 | Compound (3) | 10 | −0.05 | 15.0 |
| Sample 1-3 | Compound (4) | 8 | +0.03 | 18.6 |
| Sample 1-4 | Compound (6) | 10 | +0.10 | 13.5 |
| Sample 1-5 | Compound (9) | 9 | −0.05 | 11.0 |

*1: The sensitivity is shown by the difference as logE value with the sensitivity of Comparison Sample a as standard.
*2: The gradation is the slope of the line connecting density 0.3 and density 3.0 in the characteristic curve. The larger, the slope, the higher the gradation.

As shown in the results, it can be seen that the samples of this invention give high gradation invention as compared with Comparison Examples a and b in which Comparison Compound A and B were used, respectively.

In addition, the comparison compounds used in the example were as follows.

Comparison Compound A:

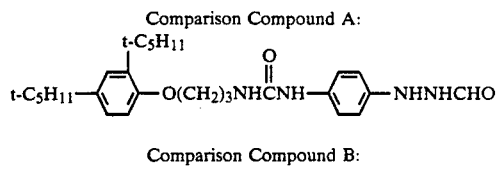

Comparison Compound B:

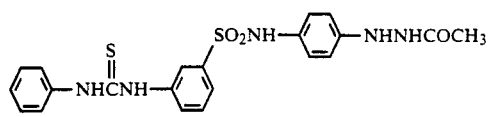

Test for Forcible Storage Stability

The aforesaid samples were aged under high temperature and high humidity conditions and then light-exposed and processed as above. Then, the photographic properties were measured and the results obtained are shown in Table 3 below.

TABLE 3

| | Fresh | | Forcible Deterioration Condition | | | |
|---|---|---|---|---|---|---|
| | | | 50° C., 65% RH, 3 days | | 50° C., 75% RH, 3 days | |
| Sample | Relative Sensitivity (S) | Gradation (γ) | ΔS* | γ | ΔS* | γ |
| Comparison Sample -a | 0 | 7.5 | −0.15 | 5.0 | −0.25 | 5.0 |
| Comparison Sample -b | +0.10 | 8.0 | +0.20 | 3.0 | +0.30 | 3.0 |
| Invention Sample 1-1 | +0.05 | 20.0 | −0.05 | 17.5 | −0.10 | 17.0 |
| Invention Sample-1-2 | −0.05 | 15.0 | −0.03 | 14.0 | −0.10 | 14.0 |
| Invention Sample 1-3 | +0.03 | 18.6 | −0.07 | 15.5 | −0.10 | 14.0 |
| Invention Sample 1-4 | +0.10 | 13.5 | −0.05 | 12.0 | −0.10 | 10.5 |
| Invention Sample 1-5 | −0.05 | 11.0 | −0.03 | 10.0 | −0.10 | 10.0 |

ΔS: The difference between the sensitititivity of fresh sample and the sensitivity of the sample after forcible stored.

As shown in the above table, it can be seen that the samples of this invention show less change of sensitivity by the forcible storage test as compared with the comparison samples.

EXAMPLE 3

Each of Light-Sensitive Element Nos. 1 to 8 was prepared by forming the following layers on a polyethylene terephthalate transparent support.

(1) A mordant layer containing 3.0 g/m² of a polymer containing the recurring unit shown below described in U.S. Pat. No. 3,898,088 and 3.0 g/m² of gelatin.

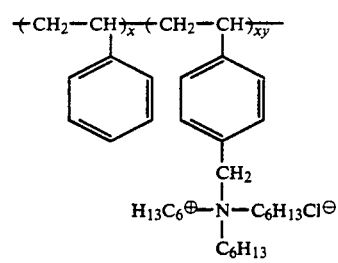

x:y = 50:50

(2) A white reflection layer containing 20 g/m² of titanium oxide and 2.0 g/m² of gelatin.

(3) A light shielding layer containing 2.70 g/m² of carbon black and 2.70 g/m² of gelatin.

(4) A layer containing 0.45 g/m² of the magenta DRR compound shown below, 0.10 g/m² of diethyllaurylamide, 0.0074 g/m² of 2,5-di-t-butylhydroquinone, and 0.76 g/m² of gelatin.

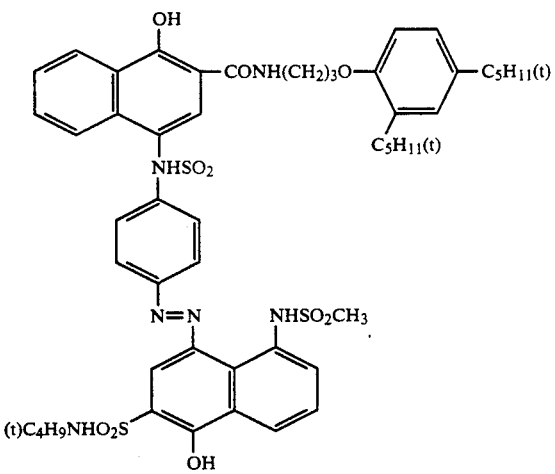

(5) An green-sensitive internal latent image type direct positive silver iodobromide emulsion layer containing an internal latent image silver iodobromide emulsion (1.4 g/m² as silver), 1.9 mg/m² of a green sensitizing dye, a nucleating agent shown in Table 3, and 0.11 g/m² of sodium 5-pentadecylhydroquinone-2-sulfonate.

(6) A layer containing 0.94 g/m² of gelatin.

Each of the light-sensitive elements was used in a combination of the following processing composition.

| Processing Composition | |
|---|---|
| 1-Phenyl-4-methyl-4-hydroxymethyl-3-pyrazolidine | 10 g |
| Methylhydroquinone | 0.18 g |
| 5-Methylbenztriazole | 4.0 g |
| Sodium Sulfite (anhydrous) | 1.0 g |
| Carboxymethyl Cellulose Sodium Salt | 40.0 g |
| Carbon Black | 150 g |
| Potassium Hydroxide (28% aq, soln.) | 200 ml |
| Water | 550 ml |

In this example, 0.8 g each of the processing composition described above was filled in a pressure rupturable container.

Cover Sheet

A cover sheet was prepared by coating a polyethylene terephthalate support with 15 g/m² of polyacrylic acid (having viscosity of 1,000 c.p. in a 10% aqueous solution thereof) as an acid polymer layer (neutralization layer) and 3.8 g/m² of acetyl cellulose (forming 39.4 g of acetyl group by the decomposition of 100 g of acetyl cellulose) and 0.2 g/m² of a styrene-maleic anhydride copolymer (styrene/maleic anhydride = about 60/40 by mole ratio, molecular weight: about 50,000) as a neutralization timing layer.

Forcible Deterioration Condition

Two sets of the aforesaid Light-Sensitive Element Nos. 1 to 8 were prepared. One set was stored in a refrigerator (5° C.) and the other set was allowed to stand for 4 days at temperature of 35° C. and relative humidity of 80%.

Processing Step

The cover sheet was superposed on each light-sensitive element described above and after exposing them to a color test chart from the cover sheet side, the aforesaid processing composition was spread between both sheets so that the thickness thereof became 75 μm by the aid of a pressure applying means.

After one hour from the processing, the green density of the image formed in the image-receiving layer was measured through the transparent sheet for the light-sensitive element by means of a Macbeth reflection densitometer. The results obtained are shown in Table 4 below.

TABLE 4

| Light-Sensitive Element No. | Nucleating Agent Kind | Amount added (mg/m²) | $D^{R*}_{max}$ | $S^{F**}$ | $S^{W***}$ |
|---|---|---|---|---|---|
| 1 (Comparison) | ExZK-1 | 0.1 | 1.17 | 100 | 100 |
| 2 (Comparison) | Comparison Compond-B | 0.5 | 1.50 | Not measurable | Not measurable |
| 3 (Invention) | (1) | 0.1 | 1.95 | 100 | 103 |
| 4 (Invention) | (2) | " | 1.93 | 99 | 103 |
| 5 (Invention) | (7) | " | 1.91 | 97 | 104 |
| 6 (Invention) | (8) | " | 1.94 | 98 | 102 |
| 7 (Invention) | (9) | " | 1.90 | 100 | 103 |
| 8 (Invention) | (14) | " | 1.97 | 99 | 104 |

In Table 4 above:
$D^{F*}_{max}$: The maximum density of the positive image portion of the sample stored in refrigerator.
$S^{F**}$: Relative sensitivity of density 0.5 of the positive image portion of the sample stored in refrigerator ($S^F$ of Light-Sensitive Element No. 1 being defined as 100).
$S^{W***}$: Relative sensivity of density 0.5 of the positive image portion of the sample stored for 4 days at 35° C. and 80% RH (that of Light-Sensitive Element No. 1 being defined as 100).

From the results shown in the above Table, it can be seen that Light-Sensitive Elements 3-8 containing the nucleating agents in this invention easily give Dmax with the same addition amount thereof as compared with Comparison Light-Sensitive Element 1 of a conventional type and also Light-Sensitive Elements 3 to 8 of this invention show less change in sensitivity with the passage of time as compared with Comparison Sample 2.

EXAMPLE 4

In the practice of this example, following Emulsion X was prepared.

Emulsion X:

An aqueous silver nitrate solution and an aqueous potassium bromide solution were simultaneously added to an aqueous gelatin solution (pH 5.5) of 75° C. containing 20 mg/liter of thioether(1,8-dihydroxy-3,6-dithiaoctane) with stirring well at same addition rate while keeping a silver electrode potential sufficient for growing regular octahedral grains at an amount of silver nitrate corresponding to ⅛ mole over a period of 5 minutes to provide a spherical silver bromide grain monodisperse emulsion having a mean grain size of about 0.14 μm.

To the emulsion were added 20 mg of sodium thiosulfate and 20 mg of chloroauric acid (tetrahydrate) per mole of silver halide and after adjusting the pH thereof to 7.5, the mixture was chemically sensitized for 80 minutes at 75° C. with stirring well to provide a core silver halide emulsion.

Then, an aqueous silver halide solution (containing 7/8 mole of silver nitrate) and an aqueous potassium bromide solution were simultaneously added to the emulsion at the same temperature with stirring while keeping the silver electrode potential of growing regular octahedral grains over a period of 40 minutes to allow for the growth of the shell. Thus, a monodisperse octahedral core/shell type silver halide emulsion having a mean grain size of about 0.3 μm was obtained.

The silver halide emulsion was washed and desalted by ordinary manners, fused by heating, and the pH thereof was adjusted to 6.5. Then, 5 mg of sodium thiosulfate and 5 mg of chloroauric acid (tetra-hydrate) per mole of silver halide were added to the emulsion followed by ripening at 75° C. for 60 minutes to perform a chemical sensitization of the shell surface. Thus, an internal latent image type monodisperse octahedral core/shell silver halide emulsion (Emulsion X) was finally obtained. The mean grain size of the silver halide grains of the emulsion measured from the electron microphotograph was 0.30 μm and the coefficient of variation (mean grain size×100/standard deviation) was 10%.

After adding a panchromatic sensitizing dye, 3,3'-diethyl-9-methylthiacarbocyanine, to Emulsion X thus prepared in an amount of 5 mg per mole of silver halide, each of Compounds (1), (3), (6) and (9) and Comparison Compound C as a nucleating agent was added in an amount shown in Table 5 below and Compound D as a nucleation accelerator was added in an amount of $1 \times 10^{-3}$ mole per mole of silver halide. The emulsion thus prepared was coated onto a polyethylene terephthalate support at a silver coverage of 2.8 g/m². In this case, a protective layer comprising gelatin and a hardening agent were simultaneously coated onto the support. Thus, a direct positive photographic light-sensitive material sensitive up to red light was obtained.

The photographic material thus prepared was exposed through a step wedge using an actinometer of tungsten lamp of 1 kW (color temperature 2854° K.) for 0.1 seconds.

Then, the photographic material was developed for 18 seconds at 38° C. using Kodak Proster Plus, processing solution (developer pH 10.7), by means of an automatic processor (Kodak Proster I Processor) and then washed, fixed, washed and dried by the same processor.

For each of the samples thus processed, the maximum density (Dmax), the minimum density (Dmix), and the relative density of the direct positive images formed were measured. The results obtained are shown in Table 5.

TABLE 5

| Sample No. | Compound Kind | Amount added (mol/AgXmol) | Positive Image (Dmax) | Positive Image (Dmin) | Relative Sensitivity (at D = 1.2) |
|---|---|---|---|---|---|
| (Comparison) 1 | Comparison Compound C | $1.0 \times 10^{-4}$ | 2.20 | 0.08 | 100 |
| (Invention) 2 | Examplified Compound (1) | $1.0 \times 10^{-5}$ | 2.62 | 0.06 | 125 |
|  |  | $2.0 \times 10^{-5}$ | 2.73 | 0.07 | 110 |
|  |  | $3.0 \times 10^{-5}$ | 2.71 | 0.07 | 115 |
| (Invention) 3 | Examplified Compound (3) | $1.0 \times 10^{-5}$ | 2.60 | 0.06 | 123 |
|  |  | $2.0 \times 10^{-5}$ | 2.68 | 0.07 | 109 |
|  |  | $3.0 \times 10^{-5}$ | 2.69 | 0.07 | 113 |
| (Invention) 4 | Examplified Compound (6) | $1.0 \times 10^{-5}$ | 2.58 | 0.06 | 120 |
|  |  | $2.0 \times 10^{-5}$ | 2.65 | 0.07 | 107 |
|  |  | $3.0 \times 10^{-6}$ | 2.64 | 0.07 | 110 |
| (Invention) 5 | Examplified Compound (9) | $1.0 \times 10^{-5}$ | 2.55 | 0.05 | 118 |
|  |  | $2.0 \times 10^{-5}$ | 2.62 | 0.06 | 105 |
|  |  | $3.0 \times 10^{-5}$ | 2.60 | 0.07 | 109 |

From the results shown in Table 5 above, it can be seen that the nucleating agents of this invention (Compounds (1), (3), (6) and (9)) show excellent reversal characteristics as compared with the case of using the control nucleating agent (Comparison Compound C) in the addition amount of 1/10 of the amount of control nucleating agent. They also show high sensitivity. That is, it can be seen that the novel nucleating agents of this invention have very high nucleating activity.

Also, when these samples were similarly developed by the developer, the pH of which was adjusted to 10.0 with acid, it was also confirmed that the samples using the nucleating agents of this invention showed excellent reversal characteristics.

Comparison Compound C:

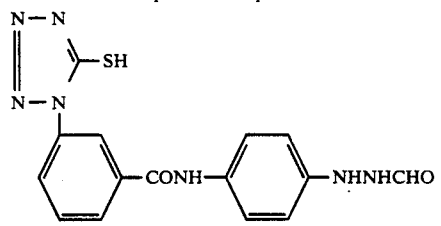

Comparison Compound D:

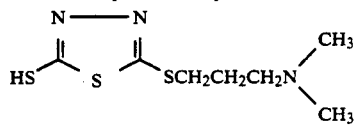

EXAMPLE 5

By following the same procedure as Example 1 except that the following nucleating agent (ExZK-201) was used, a multilayered color photographic material (Sample No. A) was prepared.

Nucleating Agent (ExZK-201):

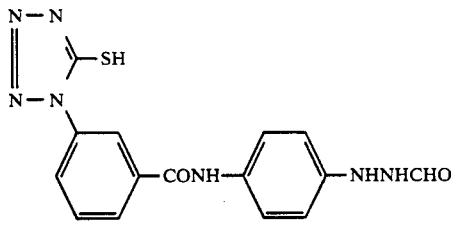

Also, by following the same procedure as above except that each of the compounds shown in Table 6 below was used in place of nucleating agent (ExZK-201), multilayered color photographic materials (Sample Nos. 1 to 13) were prepared.

Each of the samples thus prepared was wedge exposed (1/10 sec., 10 CMS), processed by Processing Step A shown in Example 1, and the density of the cyan color images formed was measured. The results obtained are shown in Table 6 below.

As shown in the above table, it can be seen that Sample Nos. 1 to 13 using the nucleating agents of this invention show higher maximum image density (Dmax) than Comparison Sample No. A. In addition, the same results were obtained for magenta density and yellow density.

TABLE 6

| | | Cyan Image Density | |
|---|---|---|---|
| No. | Nucleating Agent | Dmax | Dmin |
| 1 | Examplified Compound (1) | 1.9 | 0.11 |
| 2 | Examplified Compound (3) | 1.8 | 0.11 |
| 3 | Examplified Compound (4) | 1.9 | 0.11 |
| 4 | Examplified Compound (6) | 1.8 | 0.11 |
| 5 | Examplified Compound (7) | 1.9 | 0.11 |
| 6 | Examplified Compound (8) | 1.8 | 0.11 |
| 7 | Examplified Compound (9) | 1.8 | 0.11 |
| 8 | Examplified Compound (10) | 1.8 | 0.11 |
| 9 | Examplified Compound (13) | 1.8 | 0.11 |
| 10 | Examplified Compound (22) | 1.9 | 0.11 |
| 11 | Examplified Compound (36) | 1.9 | 0.11 |
| 12 | Examplified Compound (41) | 1.9 | 0.11 |
| 13 | Examplified Compound (42) | 1.9 | 0.11 |
| A | ExZK-201 | 1.4 | 0.12 |

TABLE 7

| | Compound | | | |
|---|---|---|---|---|
| Sample | Type | Amount added (mg/m$^2$) | Sensitivity (relative ratio) | Gradation ($\gamma$) |
| Comparison sample a | Comparison Compound A | 37 | 0 | 7.5 |
| Comparison sample b | Comparison Compound B | 12 | +0.10 | 5.0 |
| Invention sample 1-1 | Examplified Compound (222) | 8 | −0.05 | 15.7 |
| Invention sample 1-2 | Examplified Compound (236) | 9 | −0.05 | 15.2 |
| Invention sample 1-3 | Examplified Compound (240) | 10 | +0.03 | 14.3 |
| Invention sample 1-4 | Examplified Compound (241) | 10 | +0.10 | 20.5 |
| Invention sample 1-5 | Examplified Compound (242) | 8 | −0.05 | 15.0 |

Test of Forcible Storage Stability

The aforesaid samples were aged at high temperature and high humidity and similarly exposed and processed as above. Then, their photographic properties were measured. The results are shown in Table 8. The results show that the samples of this invention show less change by the forcible deterioration test as compared with the comparison samples.

TABLE 8

| | Fresh | | Forcible Deterioration Condition | | | |
|---|---|---|---|---|---|---|
| | Relative Sensitivity (S) | Gradation ($\gamma$) | 50° C., 65% RH, 3 days | | 50° C., 75% RH, 3 days | |
| Sample | | | $\Delta S^*$ | $\gamma$ | $\Delta S^*$ | $\gamma$ |
| Comparison sample a | 0 | 7.5 | −0.15 | 5.0 | −0.25 | 5.0 |
| Comparison sample b | +0.10 | 8.0 | +0.20 | 3.0 | +0.30 | 3.0 |
| Invention sample 1-1 | −0.05 | 15.7 | −0.03 | 14.1 | −0.08 | 13.9 |
| Invention sample 1-2 | −0.05 | 15.2 | −0.03 | 13.8 | −0.10 | 13.8 |
| Invention sample 1-3 | +0.03 | 14.3 | −0.07 | 12.5 | −0.10 | 11.7 |
| Invention sample 1-4 | +0.10 | 20.5 | −0.05 | 17.5 | −0.10 | 16.0 |
| Invention sample 1-5 | −0.05 | 15.0 | −0.03 | 14.0 | −0.10 | 14.0 |

EXAMPLE 6

By following the same procedure as Example 2 using the compounds shown in Table 7 below as the nucleating agents, photographic materials were prepared and the photographic properties were measured as in Example 2. The results obtained are shown in Table 7.

EXAMPLE 7

By following the same procedure as Example 3 except that each of the nucleating agents shown in Table 9 was used, photographic light-sensitive elements (Sample Nos. 1 to 8) were prepared and the same test as Example 3 was applied to these samples.

The results obtained are shown in Table 9 below.

TABLE 9

| | Nucleating Agent | | | | |
|---|---|---|---|---|---|
| Light-sensitive element No. | Type | Amount added (mg/m$^2$) | $D^F_{max}$ | $S^R$ | $S^W$ |
| 1 (Comparison) | ExZK-201 | 0.1 | 1.57 | 100 | 100 |
| 2 (Comparison) | Comparison compond-B | 0.5 | 1.51 | Not measurable | Not measurable |
| 3 (Invention) | (201) | 0.1 | 1.80 | 100 | 103 |
| 4 (Invention) | (202) | " | 1.78 | 97 | 104 |
| 5 (Invention) | (206) | " | 1.77 | 98 | 102 |

TABLE 9-continued

| Light-sensitive element No. | Nucleating Agent Type | Amount added (mg/m²) | $D^F_{max}$ | $S^R$ | $S^W$ |
|---|---|---|---|---|---|
| 6 (Invention) | (207) | " | 1.81 | 100 | 101 |
| 7 (Invention) | (209) | " | 1.79 | 99 | 102 |
| 8 (Invention) | (213) | " | 1.77 | 96 | 103 |

From the results shown in above table, it can be seen that the light-sensitive elements (Sample Nos. 3 to 8) containing the nucleating agents of this invention, used in the same amount as the comparison nucleating agent, easily provide Dmax as compared to the comparison light-sensitive element (Sample No. 1) containing a conventional nucleating agent. Also the light-sensitive elements (Sample Nos. 3 to 8) show less change of sensitivity with the passage of time as compared to the comparison sample (Sample No. 2).

EXAMPLE 8

By following the same procedure as Example 4 except that each of the nucleating agents shown in Table 10 was used, photographic materials (Sample Nos. 1 to 5) were prepared and the same test as in Example 4 was applied. The results obtained are shown in Table 10.

TABLE 10

| Sample No. | Compound Kind | Amount added (mol/AgXmol) | Positive Image Dmax | Positive Image Dmin | Relative Sensitivity (at D = 1.2) |
|---|---|---|---|---|---|
| (Comparison) | Comparison compound C | $1.0 \times 10^{-4}$ | 2.20 | 0.08 | 100 |
| (Invention) 2 | Examplified compound (236) | $1.0 \times 10^{-5}$ | 2.60 | 0.06 | 123 |
| | | $2.0 \times 10^{-5}$ | 2.70 | 0.07 | 112 |
| | | $3.0 \times 10^{-5}$ | 2.70 | 0.07 | 116 |
| (Invention) 3 | Examplified compound (240) | $1.0 \times 10^{-5}$ | 2.58 | 0.06 | 121 |
| | | $2.0 \times 10^{-5}$ | 2.67 | 0.07 | 110 |
| | | $3.0 \times 10^{-5}$ | 2.65 | 0.07 | 114 |
| (Invention) 4 | Examplified compound (241) | $1.0 \times 10^{-5}$ | 2.55 | 0.06 | 120 |
| | | $2.0 \times 10^{-5}$ | 2.65 | 0.07 | 112 |
| | | $3.0 \times 10^{-5}$ | 2.63 | 0.07 | 113 |
| (Invention) 5 | Examplified compound (242) | $1.0 \times 10^{-5}$ | 2.60 | 0.06 | 124 |
| | | $2.0 \times 10^{-5}$ | 2.71 | 0.07 | 113 |
| | | $3.0 \times 10^{-5}$ | 2.69 | 0.07 | 117 |

Also, when these samples were developed by the developer, the pH of which was adjusted to 10.0 with acid, it was confirmed that the samples of this invention show similar excellent reversal characteristics.

EXAMPLE 9

By following the same procedure as Example 1 except that the following nucleating agent was used, a multilayered color photographic material (Sample No. A) was prepared.

Nucleating Agent (ExZK-201)

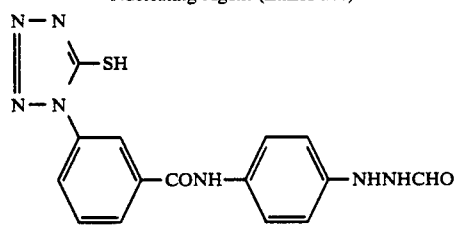

Then, by following the same procedure as above except that each of the compounds shown in Table 11 below were used in place in nucleating Agent (ExZK-201), multilayered color photographic materials (Sample Nos. 1 to 13) were prepared.

Each of the samples thus prepared was wedge-exposed (1/10 sec., 10 CMS), processed by Processing Step A of Example 1, and the density of the cyan color images formed was measured. The results obtained are shown in Table 11 below.

TABLE 11

| | | Cyan image density | |
|---|---|---|---|
| No. | Neucleating Agent | Dmax | Dmin |
| 1 | Exemplified compound (1) | 2.2 | 0.11 |
| 2 | Exemplified compound (2) | 2.1 | 0.11 |
| 3 | Exemplified compound (3) | 2.2 | 0.11 |
| 4 | Exemplified compound (5) | 2.2 | 0.11 |
| 5 | Exemplified compound (8) | 2.1 | 0.11 |
| 6 | Exemplified compound (10) | 2.1 | 0.11 |
| 7 | Exemplified compound (11) | 2.2 | 0.11 |
| 8 | Exemplified compound (12) | 2.1 | 0.11 |
| 9 | Exemplified compound (14) | 2.1 | 0.11 |
| 10 | Exemplified compound (24) | 2.1 | 0.11 |
| 11 | Exemplified compound (25) | 2.1 | 0.11 |
| 12 | Exemplified compound (31) | 2.1 | 0.11 |
| 13 | Exemplified compound (34) | 2.1 | 0.11 |
| A | ExZK-201 | 1.4 | 0.12 |

As shown in the above table, it can be seen that Sample Nos. 1 to 13 using the nucleating agents of this invention show high maximum image density (Dmax) as compared with the comparison sample (Sample No. A).

In addition, same results were obtained for the magenta desity and yellow density.

EXAMPLE 10

By following the same procedure as Example 2 except that each of the compounds shown in Table 12 was used as the nucleating agent, photographic materials were prepared and the same test as in Example 2 was applied. The results obtained are shown in Table 12. The results show the superiority of the samples of this invention.

TABLE 12

| Sample | Compound Type | Amount added (mg/m$^2$) | Sensitivity (Relative ratio) | Gradation ($\gamma$) |
|---|---|---|---|---|
| Comparison sample a | Comparison compound A* | 37 | 0 | 7.5 |
| Comparison sample b | Comparison compound B | 12 | +0.09 | 5.0 |
| Invention sample 1-1 | Exemplified compound (1) | 8 | +0.02 | 20.0 |
| Invention sample 1-2 | Exemplified compound (2) | 9 | −0.02 | 18.2 |
| Invention sample 1-3 | Exemplified compound (5) | 9 | +0.03 | 18.6 |
| Invention sample 1-4 | Exemplified compound (8) | 10 | +0.10 | 13.5 |
| Invention sample 1-5 | Exemplified compound (10) | 10 | −0.05 | 12.0 |

Test of Forcible Storage Stability

The aforesaid samples were aged at high temperature and high humidity and then exposed and processed as above. Then, the photographic properties were measured. The results obtained are shown in Table 13. From the results, it can be seen that the samples of this invention show less change by the forcible deterioration test as compared to the comparison samples.

As shown in the above table, it can be seen that the light-sensitive elements (Sample Nos. 3 to 8) containing the nucleating agents in this invention easily provide Dmax as compared with the comparison light-sensitive element (Sample No. 1) with the same addition amount the nucleating agent Sample Nos. 3 to 8 also show less change of sensitivity with the passage of time as compared with Comparison Sample No. 2.

TABLE 13

| | Fresh | | Forcible Deterioration Condition | | | |
|---|---|---|---|---|---|---|
| | Relative | | 50° C., 65% RH, 3 days | | 50° C., 75% RH, 3 days | |
| Sample | sensitivity (S) | Gradation ($\gamma$) | $\Delta$S* | $\gamma$ | $\Delta$S* | $\gamma$ |
| Comparison sample a | 0 | 7.5 | −0.15 | 5.0 | −0.25 | 5.0 |
| Comparison sample b | +0.10 | 8.0 | +0.20 | 3.0 | +0.30 | 3.0 |
| Invention sample 1-1 | +0.05 | 20.0 | −0.05 | 17.3 | −0.10 | 16.7 |
| Invention sample 1-2 | −0.02 | 18.2 | 0.00 | 15.1 | −0.04 | 15.0 |
| Invention sample 1-3 | +0.03 | 18.6 | −0.06 | 15.7 | −0.10 | 14.5 |
| Invention sample 1-4 | −0.10 | 13.5 | −0.04 | 12.5 | −0.10 | 10.7 |
| Invention sample 1-5 | −0.05 | 12.0 | −0.03 | 11.4 | −0.07 | 10.7 |

EXAMPLE 11

By following the same procedure as Example 3 using the compounds shown in Table 14 below as the nucleating agents, light sensitive elements (Sample Nos. 1 to 8) were prepared and the same test as in Example 3 was applied. The results obtained are shown in Table 14.

EXAMPLE 12

By following the same procedure as Example 4 except that the compounds shown in Table 15 below were used as the nucleating agent, photographic materials (Sample Nos. 1 to 5) were prepared and the same test as in Example 4 was applied. Then, the photographic properties of the images formed were measured. The results obtained are shown in Table 15 below.

TABLE 14

| Light-sensitive element No. | Nucleating Agent Kind | Amount added (mg/m$^2$) | $D^F_{max}$ | $S^F$ | $S^W$ |
|---|---|---|---|---|---|
| 1 (Comparison) | ExZK-1 | 0.1 | 1.72 | 100 | 100 |
| 2 (Comparison) | Comparison compond-B | 0.5 | 1.50 | Not measurable | Not measurable |
| 3 (Invention) | (1) | 0.1 | 2.00 | 97 | 104 |
| 4 (Invention) | (3) | " | 1.98 | 99 | 103 |
| 5 (Invention) | (8) | " | 1.95 | 100 | 102 |
| 6 (Invention) | (10) | " | 1.97 | 98 | 103 |
| 7 (Invention) | (25) | " | 2.10 | 97 | 104 |
| 8 (Invention) | (34) | " | 1.90 | 100 | 102 |

TABLE 15

| Sample No. | Compound Kind | Amount added (mol/AgXmol) | Positive Image Dmax | Positive Image Dmin | Relative sensitivity (at D = 1.2) |
|---|---|---|---|---|---|
| (Comparison) 1 | Comparison compound C | $1.0 \times 10^{-4}$ | 2.21 | 0.08 | 100 |
| (Invention) 2 | Exemplified compound (301) | $1.0 \times 10^{-5}$ | 2.62 | 0.06 | 125 |
| | | $2.0 \times 10^{-5}$ | 2.71 | 0.07 | 111 |
| | | $3.0 \times 10^{-5}$ | 2.69 | 0.07 | 114 |
| (Invention) 3 | Exemplified compound (305) | $1.0 \times 10^{-5}$ | 2.60 | 0.06 | 122 |
| | | $2.0 \times 10^{-5}$ | 2.68 | 0.07 | 109 |
| | | $3.0 \times 10^{-5}$ | 2.65 | 0.07 | 111 |
| (Invention) 4 | Exemplified compound (308) | $1.0 \times 10^{-5}$ | 2.58 | 0.06 | 118 |
| | | $2.0 \times 10^{-5}$ | 2.63 | 0.07 | 105 |
| | | $3.0 \times 10^{-5}$ | 2.61 | 0.07 | 110 |

TABLE 15-continued

| Sample No. | Compound Kind | Amount added (mol/AgXmol) | Positive Image Dmax | Positive Image Dmin | Relative sensitivity (at D = 1.2) |
|---|---|---|---|---|---|
| (Invention) 5 | Exemplified compound (325) | $1.0 \times 10^{-5}$ | 2.65 | 0.06 | 128 |
|  |  | $2.0 \times 10^{-5}$ | 2.74 | 0.07 | 114 |
|  |  | $3.0 \times 10^{-5}$ | 2.70 | 0.07 | 117 |

Also, when the samples were developed by the developer, the pH of which was adjusted to 10.0 with acid, it was confirmed that the samples of this invention showed similar excellent reversal characteristics.

While the invention has been described in detail and with reference to specific embodiment thereof, it will be apparent to one skilled in the art that various changes and modifications can be made therein without departing from the spirit and scope thereof.

What is claimed is:

1. A silver halide photographic material comprising a support, said support having coated thereon at least one silver halide photographic emulsion layer and at least one hydrophilic colloid layer, wherein said photographic emulsion layer or said hydrophilic colloid layer contains at least one compound represented by formula (I) or (III);

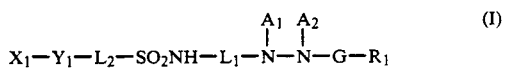

wherein $A_1$ and $R_2$ both represent a hydrogen atom or one of $A_1$ and $A_2$ represents a hydrogen atom and the other represents a sulfinic acid residue or an acyl group; $R_1$ represents a hydrogen atom, an alkyl group, an aryl group, an alkoxy group, an aralkyl group, an aryloxy group, or an amino group, further providing that these groups may be substituted; G represents a carbonyl group, a sulfonyl group, a sulfoxy group, a phosphoryl group, or an iminomethylene group which may have a N-substituent; $L_1$ represents an arylene group; $L_2$ represents a divalent linkage group; $Y_1$ represents a $-NR_2CONR_3-$ group wherein $R_2$ and $R_3$, which may be the same or different, each represents a hydrogen atom or an alkyl group, or a $-SO_2NR_4-$ group wherein $R_4$ represents a hydrogen atom or an alkyl group; and $X_1$ represents an adsorption accelerating group for silver halide, (III)

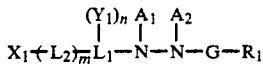

wherein $A_1$, $A_2$, $R_1$, G, $L_1$, $L_2$ and $X_1$ have the same significance as defined above as the formula (I), $Y_1$ represents a substituent capable of being dissociated into an anion having a pKa of at least 6 or an amino group, n represents 1 or 2 and m represents 0 or 1.

2. A silver halide photographic material according to claim 1, wherein said silver halide photographic emulsion layer is a negative working silver halide emulsion whereby a high contrast negative image is produced.

3. A silver halide photographic material according to claim 1, wherein said silver halide photographic emulsion layer is an internal latent image type silver halide emulsion.

4. A silver halide photographic material according to claim 3, wherein said silver halide emulsion layer comprises at least one compound represented by Formula (I).

5. A silver halide photographic material according to claim 1, wherein the total silver coating amount is from 1 g/m² to 8 g/m².

6. A silver halide photographic material according to claim 1, wherein said silver halide emulsion layer comprises an organic desensitizer.

7. A silver halide photographic material according to claim 1, wherein either said silver)halide emulsion layer or said hydrophilic colloid layer, or both, comprise one or more filter dyes and/or one or more ultraviolet absorbents.

8. A silver halide photographic material according to claim 7, wherein the amount of said filter dye and/or ultra-violet absorbents is from $10^{-2}$ g/m² to 1 g/m².

9. A silver halide photographic material according to claim 4, wherein the amount of the compound represented by Formula (I) is in the range of from about 0.005 mg to 500 mg per mol of silver in said silver halide emulsion.

10. A silver halide photographic material according to claim 9, wherein said amount is in the range of from about 0.01 mg to 100 mg per mol of silver in said silver halide emulsion.

11. A silver halide photographic material according to claim 1, wherein said compound is represented by Formula (I), which is Compound (1)

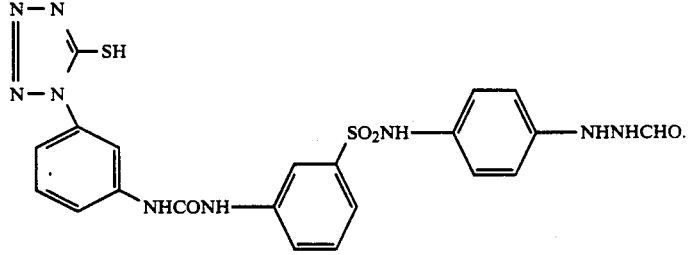

12. A silver halide photographic material according to claim 1, wherein said compound is represented by Formula 24, which is Compound (2)

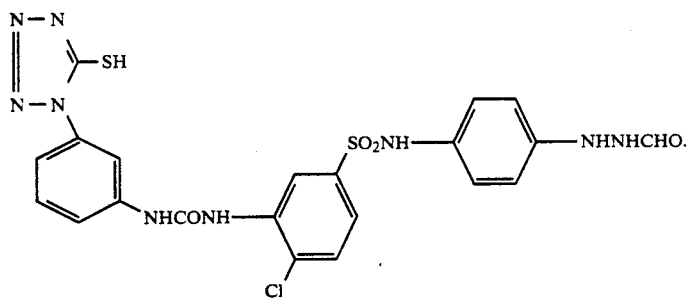

13. A silver halide photographic material according to claim 1, wherein said compound is represented by Formula 24, which is Compound (4)

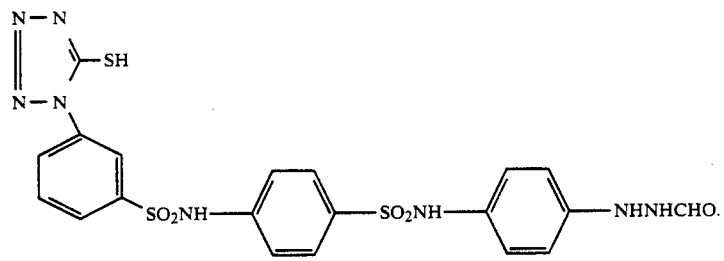

14. A silver halide photographic material according to claim 1, wherein said compound is represented by Formula 24, which is Compound (5)

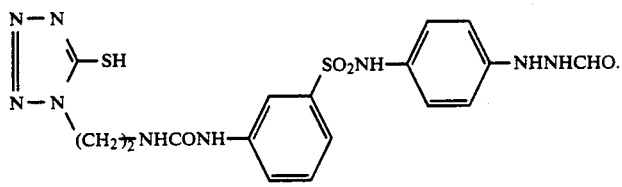

15. A silver halide photographic material according to claim 1, wherein said compound is represented by Formula 24, which is Compound (6)

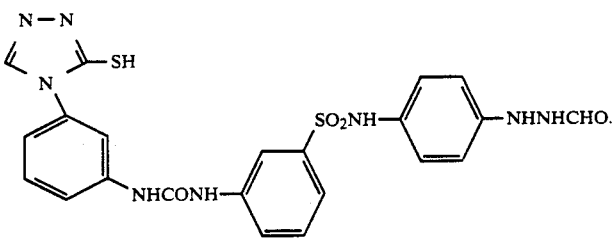

16. A silver halide photographic material according to claim 1, wherein said compound is represented by Formula 24, which is Compound (7)

-continued

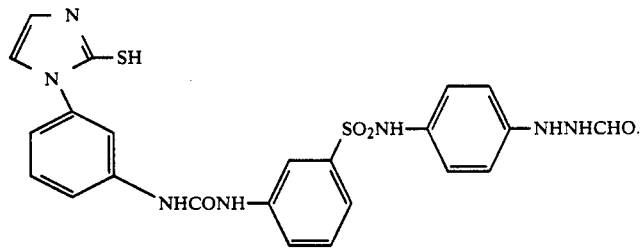

17. A silver halide photographic material according to claim 1, wherein said compound is represented by Formula 24, which is Compound (8)

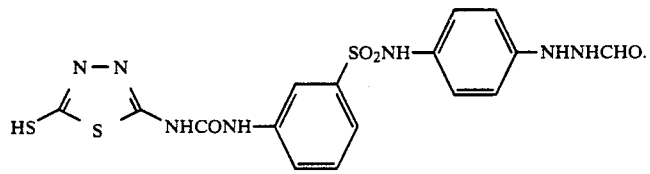

18. A silver halide photographic material according to claim 1, wherein said compound is represented by Formula 24, which is Compound (9)

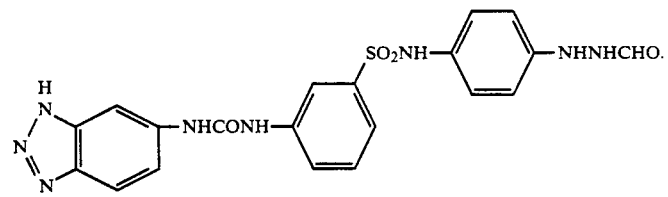

19. A silver halide photographic material according to claim 1, wherein said compound is represented by Formula 24, which is Compound (10)

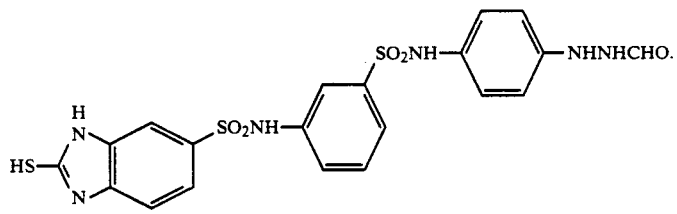

20. A silver halide photographic material according to claim 1, wherein said compound is represented by Formula 24, which is Compound (14)

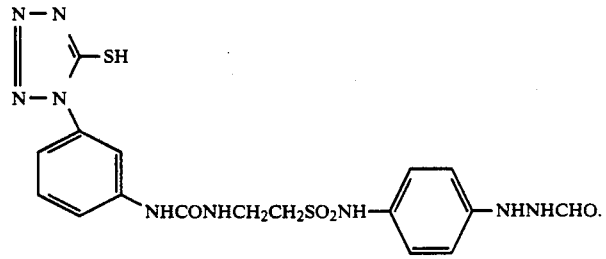

21. A silver halide photographic material according to claim 1, wherein said compound is represented by Formula 24, which is Compound (16)
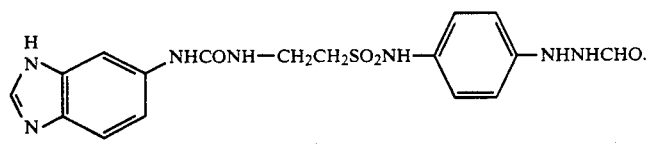
22. A silver halide photographic material according to claim 1, wherein said compound is represented by
Compound (17)
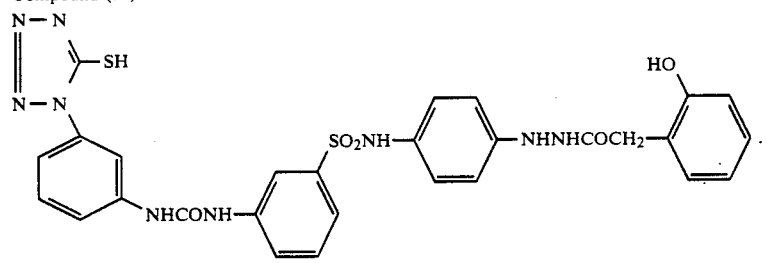
23. A silver halide photographic material according to claim 1, wherein said compound is represented by Formula 24, which is
Compound (18)
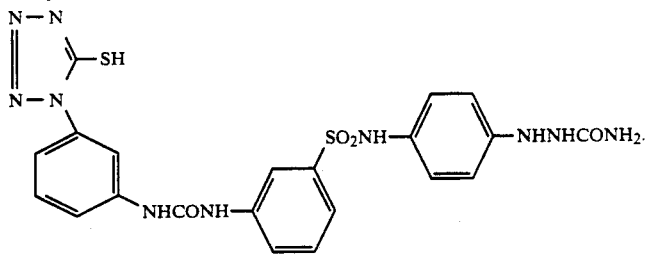
Formula 24, which is
* * * * *